(12) United States Patent
Bourque et al.

(10) Patent No.: US 9,694,123 B2
(45) Date of Patent: Jul. 4, 2017

(54) METHODS AND SYSTEMS FOR CONTROLLING A BLOOD PUMP

(71) Applicant: Thoratec Corporation, Pleasanton, CA (US)

(72) Inventors: Kevin Bourque, Reading, MA (US); Brian Kimball, Medford, MA (US); Charles P. Dague, Windham, NH (US)

(73) Assignee: TC1 LLC, St. Paul, MN (US)

(*) Notice: Subject to any disclaimer, the term of this patent is extended or adjusted under 35 U.S.C. 154(b) by 0 days.

(21) Appl. No.: 14/687,643

(22) Filed: Apr. 15, 2015

(65) Prior Publication Data

US 2015/0290374 A1    Oct. 15, 2015

Related U.S. Application Data

(60) Provisional application No. 61/979,840, filed on Apr. 15, 2014.

(51) Int. Cl.
*A61N 1/362* (2006.01)
*A61M 1/10* (2006.01)
*A61M 1/12* (2006.01)

(52) U.S. Cl.
CPC ........ *A61M 1/1086* (2013.01); *A61M 1/1029* (2014.02); *A61M 1/122* (2014.02);
(Continued)

(58) Field of Classification Search
CPC .... A61M 1/122; A61M 1/127; A61M 1/1005; A61M 1/1029; A61M 1/1086;
(Continued)

(56) References Cited

U.S. PATENT DOCUMENTS 3,240,207 A   3/1966   Barker et al.
4,190,057 A   2/1980   Downie et al.
(Continued)

FOREIGN PATENT DOCUMENTS

EP   2298375   3/2011
GB   2152241   7/1985
(Continued)

OTHER PUBLICATIONS

International Search Report from PCT/US21015/026026, dated Jul. 13, 2015.
(Continued)

*Primary Examiner* — Mallika D Fairchild
(74) *Attorney, Agent, or Firm* — Kilpatrick Townsend & Stockton LLP

(57) ABSTRACT

The present invention generally relates to ventricular assist device power monitoring and conservation. In some embodiments, a pump controller may transition the pump to operate in a power-saving operational mode when a power source and/or a power source condition indicate a need to conserve power. In some embodiments, when the power source is an emergency battery and when the emergency battery has powered the pump for an extended period of time, the controller may signal the pump to operate in the power saving-operational mode. In some embodiments, when a low power hazard condition is triggered by signals from one or more external power sources, the controller may signal the pump to transition to the power-saving operational mode if the condition lasts for an extended period of time. In some embodiments, the controller may trigger the power-saving mode when the emergency backup battery is below a voltage threshold.

38 Claims, 11 Drawing Sheets

(52) U.S. Cl.
CPC ..... *A61M 1/127* (2013.01); *A61M 2205/3334* (2013.01); *A61M 2205/50* (2013.01); *A61M 2205/8212* (2013.01); *A61M 2205/8262* (2013.01)

(58) Field of Classification Search
CPC .. A61M 2205/8262; A61M 2205/8212; A61M 2205/3334; A61M 2205/50; A61M 2205/14
See application file for complete search history.

(56) References Cited

U.S. PATENT DOCUMENTS

| | | | |
|---|---|---|---|
| 4,296,500 | A | 10/1981 | Monties et al. |
| 4,600,855 | A | 7/1986 | Strachan |
| 4,957,504 | A | 9/1990 | Chardack |
| 5,279,292 | A | 1/1994 | Baumann et al. |
| 5,289,821 | A | 3/1994 | Swartz |
| 5,385,581 | A | 1/1995 | Bramm et al. |
| 5,658,318 | A | 8/1997 | Stroetmann et al. |
| 5,693,091 | A | 12/1997 | Larson, Jr. et al. |
| 5,695,471 | A | 12/1997 | Wampler |
| 5,708,346 | A | 1/1998 | Schöb |
| 5,715,837 | A | 2/1998 | Chen |
| 5,725,357 | A | 3/1998 | Nakazeki et al. |
| 5,798,454 | A | 8/1998 | Nakazeki et al. |
| 5,807,258 | A | 9/1998 | Cimochowski et al. |
| 5,888,242 | A | 3/1999 | Antaki et al. |
| 5,947,703 | A | 9/1999 | Nojiri et al. |
| 6,027,498 | A | 2/2000 | Mutch et al. |
| 6,048,363 | A | 4/2000 | Nagyszalanczy et al. |
| 6,053,705 | A | 4/2000 | Schöb et al. |
| 6,053,873 | A | 4/2000 | Govari et al. |
| 6,066,086 | A | 5/2000 | Antaki et al. |
| 6,071,093 | A | 6/2000 | Hart |
| 6,100,618 | A | 8/2000 | Schoeb et al. |
| 6,116,862 | A | 9/2000 | Rau et al. |
| 6,142,752 | A | 11/2000 | Akamatsu et al. |
| 6,146,325 | A | 11/2000 | Lewis et al. |
| 6,171,253 | B1 | 1/2001 | Bullister et al. |
| 6,176,822 | B1 | 1/2001 | Nix et al. |
| 6,183,412 | B1 * | 2/2001 | Benkowski ........... A61M 1/101 600/16 |
| 6,186,665 | B1 | 2/2001 | Maher et al. |
| 6,222,290 | B1 | 4/2001 | Schöb et al. |
| 6,234,772 | B1 | 5/2001 | Wampler et al. |
| 6,249,067 | B1 | 6/2001 | Schob et al. |
| 6,264,601 | B1 | 7/2001 | Jassawalla et al. |
| 6,264,635 | B1 | 7/2001 | Wampler et al. |
| 6,277,078 | B1 | 8/2001 | Porat et al. |
| 6,278,251 | B1 | 8/2001 | Schöb |
| 6,293,901 | B1 | 9/2001 | Prem |
| 6,351,048 | B1 | 2/2002 | Schob et al. |
| 6,355,998 | B1 | 3/2002 | Schöb et al. |
| 6,367,333 | B1 | 4/2002 | Bullister et al. |
| 6,395,027 | B1 | 5/2002 | Snyder |
| 6,409,674 | B1 | 6/2002 | Brockway et al. |
| 6,422,990 | B1 | 7/2002 | Prem |
| 6,443,884 | B1 | 9/2002 | Miyawaki |
| 6,468,041 | B2 | 10/2002 | Ozaki |
| 6,481,292 | B1 | 11/2002 | Reich |
| 6,540,658 | B1 | 4/2003 | Fasciano et al. |
| 6,547,753 | B1 | 4/2003 | Plunkett et al. |
| 6,575,717 | B2 | 6/2003 | Ozaki et al. |
| 6,589,030 | B2 | 7/2003 | Ozaki |
| 6,605,032 | B2 | 8/2003 | Benkowski et al. |
| 6,623,420 | B2 | 9/2003 | Reich et al. |
| 6,626,644 | B2 | 9/2003 | Ozaki |
| 6,634,224 | B1 | 10/2003 | Schöb et al. |
| 6,636,769 | B2 | 10/2003 | Govari et al. |
| 6,669,624 | B2 | 12/2003 | Frazier |
| 6,688,861 | B2 | 2/2004 | Wampler |
| 6,707,200 | B2 | 3/2004 | Carroll et al. |
| 6,716,189 | B1 | 4/2004 | Jarvik et al. |
| 6,736,980 | B2 | 5/2004 | Moscaritolo |
| 6,742,999 | B1 | 6/2004 | Nüsser et al. |
| 6,817,836 | B2 | 11/2004 | Nose et al. |
| 6,879,074 | B2 | 4/2005 | Amrhein et al. |
| 6,890,303 | B2 | 5/2005 | Fitz |
| 6,949,066 | B2 | 9/2005 | Bearnson et al. |
| 6,969,345 | B2 | 11/2005 | Jassawalla et al. |
| 6,974,436 | B1 | 12/2005 | Aboul-Hosn et al. |
| 6,991,595 | B2 | 1/2006 | Burke et al. |
| 7,112,903 | B1 | 9/2006 | Schob |
| 7,138,776 | B1 | 11/2006 | Gauthier et al. |
| 7,147,604 | B1 | 12/2006 | Allen et al. |
| 7,150,711 | B2 | 12/2006 | Nüsser et al. |
| 7,160,242 | B2 | 1/2007 | Yanai |
| 7,175,588 | B2 | 2/2007 | Morello |
| 7,211,048 | B1 | 5/2007 | Najafi et |
| 7,229,474 | B2 | 6/2007 | Hoffmann et al. |
| 7,239,098 | B2 | 7/2007 | Masino |
| 7,284,956 | B2 | 10/2007 | Nose et al. |
| 7,396,327 | B2 | 7/2008 | Morello |
| 7,462,019 | B1 | 12/2008 | Allarie et al. |
| 7,497,116 | B2 | 3/2009 | Miyakoshi et al. |
| 7,511,443 | B2 | 3/2009 | Townsend et al. |
| 7,578,782 | B2 | 8/2009 | Miles et al. |
| 7,591,777 | B2 | 9/2009 | LaRose |
| 7,645,225 | B2 | 1/2010 | Medvedev et al. |
| 7,645,255 | B2 | 1/2010 | Gordon et al. |
| 7,699,586 | B2 | 4/2010 | LaRose et al. |
| 7,699,588 | B2 | 4/2010 | Mendler |
| 7,850,594 | B2 | 12/2010 | Sutton et al. |
| 7,854,631 | B2 | 12/2010 | Townsendl et al. |
| 7,861,582 | B2 | 1/2011 | Miyakoshi et al. |
| 7,887,479 | B2 | 2/2011 | LaRose et al. |
| 7,951,062 | B2 | 5/2011 | Morello |
| 7,963,905 | B2 | 6/2011 | Salmonsen et al. |
| 7,976,271 | B2 | 7/2011 | LaRose et al. |
| 7,997,854 | B2 | 8/2011 | LaRose et al. |
| 8,007,254 | B2 | 8/2011 | LaRose et al. |
| 8,123,669 | B2 | 2/2012 | Siess et al. |
| 8,152,493 | B2 | 4/2012 | LaRose et al. |
| 8,157,720 | B2 | 4/2012 | Marseille et al. |
| 8,303,482 | B2 | 11/2012 | Schima et al. |
| 8,323,174 | B2 | 12/2012 | Jeevanandam et al. |
| 8,382,830 | B2 | 2/2013 | Maher et al. |
| 8,449,444 | B2 | 5/2013 | Poirier |
| 8,506,470 | B2 | 8/2013 | Larose et al. |
| 8,506,471 | B2 | 8/2013 | Bourque |
| 8,517,699 | B2 | 8/2013 | Horvath |
| 8,556,795 | B2 | 10/2013 | Bolyard et al. |
| 8,562,508 | B2 * | 10/2013 | Dague .................... A61M 1/12 600/16 |
| 8,597,350 | B2 | 12/2013 | Rudser et al. |
| 8,652,024 | B1 | 2/2014 | Yanai et al. |
| 8,657,733 | B2 | 2/2014 | Ayre et al. |
| 8,657,875 | B2 | 2/2014 | Kung et al. |
| 8,668,473 | B2 | 3/2014 | LaRose et al. |
| 8,764,621 | B2 | 7/2014 | Badstibner et al. |
| 8,870,739 | B2 | 10/2014 | Larose et al. |
| 8,882,477 | B2 | 11/2014 | Fritz, IV et al. |
| 8,956,275 | B2 | 2/2015 | Bolyard et al. |
| 8,961,388 | B2 | 2/2015 | Bourque |
| 9,011,312 | B2 | 4/2015 | Bourque |
| 2003/0199727 | A1 | 10/2003 | Burke et al. |
| 2005/0071001 | A1 | 3/2005 | Jarvik |
| 2005/0131271 | A1 | 6/2005 | Benkowski et al. |
| 2006/0241335 | A1 | 10/2006 | Benkowski et al. |
| 2007/0073393 | A1 | 3/2007 | Kung et al. |
| 2007/0078293 | A1 | 4/2007 | Shambaugh, Jr. et al. |
| 2007/0083077 | A1 | 4/2007 | Frazier |
| 2008/0021394 | A1 | 1/2008 | LaRose et al. |
| 2009/0099406 | A1 | 4/2009 | Salmonsen et al. |
| 2009/0138080 | A1 | 5/2009 | Siess et al. |
| 2009/0203957 | A1 | 8/2009 | LaRose et al. |
| 2010/0130809 | A1 | 5/2010 | Morello |
| 2010/0152526 | A1 | 6/2010 | Pacella et al. |
| 2010/0222635 | A1 | 9/2010 | Poirier |
| 2010/0241223 | A1 * | 9/2010 | Lee ..................... A61M 1/127 623/3.27 |
| 2010/0327687 | A1 | 12/2010 | Iannello et al. |
| 2011/0054239 | A1 | 3/2011 | Sutton et al. |

(56) References Cited

U.S. PATENT DOCUMENTS

| | | |
|---|---|---|
| 2011/0071337 A1 | 3/2011 | Thompson et al. |
| 2011/0112354 A1 | 5/2011 | Nishimura et al. |
| 2011/0178361 A1 | 7/2011 | Yomtov |
| 2011/0237863 A1 | 9/2011 | Ricci et al. |
| 2011/0313237 A1 | 12/2011 | Miyakoshi et al. |
| 2012/0046514 A1* | 2/2012 | Bourque ............ A61M 1/101 600/16 |
| 2012/0078030 A1* | 3/2012 | Bourque ............ A61M 1/1086 600/16 |
| 2012/0078031 A1 | 3/2012 | Burke et al. |
| 2012/0095281 A1 | 4/2012 | Reichenbach et al. |
| 2012/0226097 A1 | 9/2012 | Smith et al. |
| 2012/0226350 A1 | 9/2012 | Rudser et al. |
| 2012/0245681 A1 | 9/2012 | Casas et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0289336 A1 | 10/2013 | Bourque |
| 2013/0314047 A1 | 11/2013 | Eagle et al. |
| 2013/0331934 A1 | 12/2013 | Kabir et al. |
| 2014/0012067 A1 | 1/2014 | Poirier |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0275727 A1 | 9/2014 | Bonde et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |
| 2015/0148587 A1 | 5/2015 | Bourque |
| 2015/0151032 A1 | 6/2015 | Voskoboynikov et al. |

FOREIGN PATENT DOCUMENTS

| | | |
|---|---|---|
| JP | 04504673 | 8/1992 |
| JP | 09276397 | 10/1997 |
| JP | 2002224066 | 8/2002 |
| JP | 2003501180 | 1/2003 |
| JP | 2004510482 | 4/2004 |
| JP | 2005514962 | 5/2005 |
| JP | 2009297174 | 12/2009 |
| WO | 0076288 | 12/2000 |
| WO | 0076822 | 12/2000 |
| WO | 0172352 | 10/2001 |
| WO | 2005051838 | 6/2005 |
| WO | 2006133409 | 12/2006 |
| WO | 2009150893 | 12/2009 |

OTHER PUBLICATIONS

Written Opinion from PCT/US21015/026026, dated Jul. 13, 2015.

Fukamachi et al., "An innovative, sensorless, pulsatile, continuous-flow total artificial heart: device design and initial in vitro study", The Journal of Heart and Lung Transplantation, vol. 29, No. 1 (Jan. 2010), pp. 13-20.

Ising et al., "Flow Modulation Algorithms for Continuous Flow Left Ventricular Assist Devices to Increase Vascular Pulsatility: A Computer Simulation Study", Cardiovascular Engineering and Technology, vol. 2, No. 2 (Mar. 26, 2011), pp. 90-100.

Khalil et al., "Induced pulsation of a continuous-flow total artificial heart in a mock circulatory system", The Journal of Heart and Lung Transplantation, vol. 29, No. 5, (May 2010), pp. 568-573.

Shi et al., "Numerical modeling of hemodynamics with pulsatile impeller pump support", Annals of Biomedical Engineering, vol. 38, No. 8 (published online Mar. 16, 2010)., Aug. 2010.

Shi et al., "Numerical simulation of cardiovascular dynamics with left heart failure and in-series pulsatile ventricular assist device", Artificial Organs, vol. 30, No. 12 (2006), pp. 929-948.

Shiose et al., "Speed Modulation of the Continuous-Flow Total Artificial Heart to Simulate a Physiologic Arterial Pressure Waveform", ASAIO Journal, vol. 56, Issue 5 (Sep./Oct. 2010), pp. 403-409.

Travis et al., "Vascular pulsatility in patients with a pulsatile- or continuous-flow ventricular assist device", Journal of Thoracis and Cardiovascular Surgery, vol. 133, No. 2, (Feb. 2007), pp. 517-524.

Vandenberghe et al., "Hemodynamic modes of ventricular assist with a rotary blood pump: continuous, pulsatile, and failure", ASAIO Journal, vol. 51, Issue 6 (Nov./Dec. 2005), pp. 711-718.

\* cited by examiner

|  |  | Black Cable Status | | | | |
|---|---|---|---|---|---|---|
|  |  | Power Cable Disconnected (F7) | Unknown (F13) | Red (F9, F15) | Yellow (F11, F53) | Green |
| White Cable Status | Power Cable Disconnected (F6) | No External Power + Power Cable Disconnect (A4) | Power Cable Disconnect + Low Power Hazard (A12) | Power Cable Disconnect + Low Power Hazard (A13) | Power Cable Disconnect + Low Power Hazard (A15) | Power Cable Disconnect + Low Power Advisory (A22) |
|  | Unknown (F12) | Power Cable Disconnect + Low Power Hazard (A12) | Power Cable Disconnect + Low Power Hazard (A12) | Power Cable Disconnect + Low Power Hazard (A13) | Power Cable Disconnect + Low Power Hazard (A15) | Power Cable Disconnect + Low Power Advisory (A22) |
|  | Red (F8, F14) | Power Cable Disconnect + Low Power Hazard (A14) | Power Cable Disconnect + Low Power Hazard (A14) | Low Power Hazard (A11) | Low Power Hazard (A9) | Low Power Advisory (A23) |
|  | Yellow (F10, F52) | Power Cable Disconnect + Low Power Hazard (A16) | Power Cable Disconnect + Low Power Hazard (A16) | Low Power Hazard (A10) | Low Power Advisory (A20) | Low Power Advisory (A25) |
|  | Green | Power Cable Disconnect + Low Power Advisory (A21) | Power Cable Disconnect + Low Power Advisory (A21) | Low Power Advisory (A24) | Low Power Advisory (A25) | No Alarm |

FIG. 14

METHODS AND SYSTEMS FOR CONTROLLING A BLOOD PUMP

CROSS REFERENCE TO RELATED APPLICATION DATA

The present application claims the benefit under 35 USC §119(e) of U.S. Provisional Appln. No. 61/979,840 filed Apr. 15, 2014. The full disclosure which is incorporated herein by reference in its entirety for all purposes.

FIELD OF THE INVENTION

This description relates to generating an artificial pulse, and more specifically to methods and systems for power saving and disabling pulsatility.

BACKGROUND OF THE INVENTION

This application relates generally to mechanical circulatory support systems, and more specifically relates to power management systems and methods for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while the patient awaits a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source outside the patient's body.

While many advances have been made to supplement and/or replace heart function, further improvements may be desired that improve the duration of VAD operation when powered by portable power sources.

BRIEF SUMMARY OF THE INVENTION

The present invention provides improved systems, methods, and devices which can advantageously sustain VAD operation during low power conditions. Improving the duration of VAD operation during low power has many advantages, such as patient safety, as discussed herein. For example, identifying a mode to conserve power and transitioning from a first operational mode (e.g., pulsatility mode) to a second operation mode (e.g., steady-state) to save on power reserves allows the VAD to continue to operate uninterrupted for longer durations of time while the patient safely secures alternative power sources or recharges existing power sources. Still further, the present invention finds applicability with both external power sources and fully implantable transcutaneous energy transfer systems.

In one general aspect, a continuous flow blood pump can be operated to provide pulsatile blood flow. The motor speed for the pump can be modulated in a repeating cycle that includes a sequence of two or more speed levels. Operation of the pump can produce pressure changes that imitate a rate of pressure change of a natural physiologic pulse.

In another general aspect, pumping blood in a pulsatile manner includes operating a blood pump at a first speed for a first period of time, reducing the speed of the blood pump from the first speed to a second speed, operating the blood pump at the second speed for a second period of time, reducing the speed of the blood pump from the second speed to a third speed, operating the blood pump at the third speed for a third period of time, and increasing the speed of the blood pump from the third speed to the first speed.

Implementations can include one or more of the following features. For example, increasing the speed of the blood pump from the third speed to the first speed includes increasing the speed of the blood pump from the third speed to a fourth speed, operating the blood pump at the fourth speed for a fourth period of time, and increasing the speed of the blood pump from the fourth speed to the first speed. The second period of time is longer than a sum of the first period of time and the third period of time. Operating the blood pump at the first speed, reducing the speed of the blood pump from the first speed to the second speed, operating the blood pump at the second speed, reducing the speed of the blood pump from the second speed to the third speed, operating the blood pump at the third speed, and increasing the speed of the blood pump from the third speed to the first speed comprise a cycle, and pumping blood in a pulsatile manner further includes repeating the cycle. The duration of the second period of time is greater than half of the duration of the cycle. Operating the blood pump at the second speed for the second period of time includes operating the blood pump to produce a blood flow rate that has a predetermined relationship relative to an average blood flow rate for the cycle. Operating the blood pump at the second speed for the second period of time includes operating the blood pump to produce a blood flow substantially the same as the average blood flow rate for the cycle.

One or more of reducing the speed of the blood pump from the first speed to a second speed, reducing the speed of the blood pump from the second speed to a third speed, and increasing the speed of the blood pump from the third speed to the first speed includes one or more of a step-wise reduction in speed and a curvilinear reduction in speed. Operating the blood pump at the second speed includes operating the blood pump at the second speed during at least a portion of a contraction of a ventricle of human heart that is in blood flow communication with the blood pump. Pumping blood in a pulsatile manner also includes determining, based on a relationship between a speed of the blood pump and a power consumption of the blood pump, a synchronization between operating the impeller at the second speed and contraction of a ventricle of a human heart that is in blood flow communication with the blood pump. A generated pulsatile blood flow includes a temporal rate of change of blood pressure that approximates a temporal rate of change of blood pressure of a physiologic pulse. One or more of reducing the speed of the blood pump from the first speed to a second speed, reducing the speed of the blood pump from the second speed to a third speed, and increasing the speed of the blood pump from the third speed to the first speed includes generating a drive signal at a first time to produce a corresponding change in operating speed at a desired time. The second period of time is greater than the first period of time.

In another general aspect, a blood pump controller includes a waveform generator to generate a waveform for operating a blood pump, and a drive waveform transmitter to supply the generated drive waveform to the blood pump. The generated waveform is configured to operate a blood pump at a first speed for a first period of time, reduce the speed of the blood pump from the first speed to a second speed, operate the blood pump at the second speed for a second period of time, reduce the speed of the blood pump from the second speed to a third speed, operate the blood pump at the third speed for a third period of time, and increase the speed of the blood pump from the third speed to the first speed.

Implementations can include one or more of the following features. For example, increasing the speed of the blood pump from the third speed to the first speed includes increasing the speed of the blood pump from the third speed to a fourth speed, operating the blood pump at the fourth speed for a fourth period of time, and increasing the speed of the blood pump from the fourth speed to the first speed. The second period of time is longer than a sum of the first period of time and the third period of time. Operating the blood pump at the first speed, reducing the speed of the blood pump from the first speed to the second speed, operating the blood pump at the second speed, reducing the speed of the blood pump from the second speed to the third speed, operating the blood pump at the third speed, and increasing the speed of the blood pump from the third speed to the first speed comprise a cycle, and wherein the generated waveform is configured to repeat the cycle. The duration of the second period of time is greater than half of the duration of the cycle. Operating the blood pump at the second speed for the second period of time includes operating the blood pump to produce a blood flow rate that has a predetermined relationship relative to an average blood flow rate for the cycle. Operating the blood pump at the second speed for the second period of time includes operating the blood pump to produce a blood flow substantially the same as the average blood flow rate for the cycle.

The generated waveform is configured to change the speed of the blood pump via one or more of a step-wise change in speed and a curvilinear change in speed. The generated waveform operates the blood pump at the second speed during a contraction of a ventricle of a human heart that is in blood flow communication with the blood pump. The blood pump controller further includes a processor configured to determine, based on a relationship between a speed of the blood pump and a power consumption of the blood pump, a synchronization between operating the blood pump at the second speed and a contraction of a ventricle of a human heart that is in blood flow communication with the blood pump. The generated waveform drives the blood pump to generate a temporal rate of change of blood pressure that approximates a temporal rate of change of blood pressure of a physiologic pulse. The generated waveform is further configured to produce a corresponding change in pump operating speed at a desired time. The second period of time is greater than the first period of time.

In another general aspect, producing a pulsatile blood flow having a relatively low pressure portion and a relatively high pressure portion and having a rate of pressure change that mimics a rate of pressure change of a natural physiologic pulse includes operating a continuous flow blood pump to produce a first blood flow rate through the continuous flow blood pump associated with the relatively low pressure portion of the pulsatile blood flow, operating the continuous flow blood pump to produce a second blood flow rate through the continuous flow blood pump associated with the relatively high pressure portion of the pulsatile blood flow, and controlling the continuous flow blood pump to increase a blood flow rate through the continuous flow blood pump from the first flow rate to the second flow rate to produce the rate of pressure change that mimics the rate of pressure change of the natural physiologic pulse.

Implementations can include one or more of the following features. For example, operating the continuous blood flow pump to produce the second blood flow rate can include operating the continuous blood flow pump at a first operating speed, and controlling can include operating the continuous blood flow pump at a second operating speed, the second operating speed being associated with a third blood flow rate, the third blood flow rate being greater than the second blood flow rate. Operating the continuous flow blood pump to produce the second blood flow rate includes operating the continuous flow blood pump to produce the second blood flow rate such that the relatively high pressure portion has a duration that is longer than a duration of the relatively low pressure portion. Repeating a cycle in which the duration of the relatively high pressure portion is greater than half of the duration of the cycle. The cycle includes operating the continuous flow blood pump to produce the first blood flow rate, operating the continuous flow blood pump to produce the second blood flow rate, and controlling the continuous flow blood pump to increase the blood flow rate. Operating the continuous flow blood pump to produce the second blood flow rate includes operating the continuous flow blood pump to produce the second blood flow rate such that the second blood flow rate has a predefined relationship with an average blood flow rate of the pulsatile blood flow. The second blood flow rate is substantially equal to an average blood flow rate of the pulsatile blood flow. Controlling the continuous flow blood pump to increase the blood flow rate includes controlling the continuous flow blood pump to increase the blood flow rate through the continuous flow blood pump from the first flow rate to the second flow rate such that the blood flow rate through the continuous flow blood pump overshoots the second flow rate to produce the rate of pressure change that mimics the rate of pressure change of the natural physiologic pulse.

In many embodiments, a method for controlling an implantable blood pump with a controller is provided. The method may include identifying a status of one or more power sources for the implantable blood pump that is indicative of a need or mode to conserve power. Thereafter, the method may include transmitting a signal to the blood pump from the controller to transition from a pulsatile pumping operation to a constant speed operation. The constant speed operation may consume less power than the pulsatile pumping operation.

Identifying the status of the one or more power sources may include identifying a disconnection between the controller and one or more external power sources or a low power hazard condition status. In some embodiments, identifying the status of the one or more power sources comprises identifying a duration of time in which the controller is disconnected from the external power source or a duration of time in which the pump is operated with the low power hazard condition. The duration of time may be compared to a threshold time period. The signal may be transmitted to the blood pump when the duration of time exceeds the threshold time period. Optionally, the threshold time period may be at least 5 minutes, 10 minutes or more, or the like. In some embodiments the threshold time period is at least 15 minutes.

A low power hazard condition may be identified by monitoring a status of a first cable and a second cable coupled to the controller of the blood pump. The first cable and the second cable may be assigned: a first fault status when: 1) relative state of charge information associated with the respective cable is indicative of a rechargeable battery power source below a first threshold charge, or 2) relative state of charge information associated with the respective cable is indicative of a power module and voltage information is below a first power module threshold voltage; a second fault status when: 1) relative state of charge information associated with the respective cable is indicative of a rechargeable battery power source below a second threshold charge (the second threshold charge being lower than the first threshold charge), or 2) relative state of charge information associated with the respective cable is indicative of a rechargeable battery power source and voltage information is below a battery threshold voltage, or 3) relative state of charge information associated with the respective cable is indicative of a power module and voltage information is below a second power module threshold voltage (the second power module threshold voltage being lower than the first power module threshold voltage); an unknown fault status when relative state of charge of the respective cable is indicative of an unknown power source; a disconnect fault status when voltage information associated with the respective cable is indicative of a disconnected cable; and a third status when the first cable or second cable are not assigned a first fault status, a second fault status, an unknown fault status, or a disconnect fault status.

In some embodiments, the low power hazard condition may be triggered when the first cable is assigned the first fault status, the second fault status, or the unknown fault status, while the second cable is assigned the disconnect fault status, the unknown fault status, or the second fault status.

In further embodiments, the method may further include transmitting a second signal to the blood pump to transition back to the pulsatile pumping operation when the first cable or second cable is assigned the third status or when the first cable and the second cable are assigned the second fault status.

Optionally, the status of the power source may be identified by identifying the power source as an emergency battery which has powered the pump for greater than a threshold time period. The threshold time period may be 5 minutes or more, 10 minutes or more. In some embodiments the time period may be at least 15 minutes.

In some embodiments, the status of the power source may be identified by identifying the power source as an emergency battery which is below a threshold voltage. The threshold voltage may be equal to or less than 10.4 volts, for example.

In other aspects, a method of controlling an implantable blood pump with a controller is provided. The method may include, determining/classifying/categorizing one or more power sources with the controller and identifying an operating condition associated with the determined implantable blood pump power source that is indicative of a need to conserve power. A signal may be transmitted to the implantable blood pump from the controller to transition the implantable blood pump from a first operational mode to a second operational mode when the identified operating condition is indicative of the need to conserve power. The second operational mode may be configured to consume less power than the first operational mode. In some embodiments, the second operational mode may be configured to provide a lower flow rate, a constant speed, or the like.

In some embodiments, the method may determine that the one or more power sources is an emergency battery housed within the controller. The method may make the determination when the controller is disconnected from external power sources.

Optionally, the operating condition associated with the emergency battery that is indicative of the need to conserve power may comprise a voltage of the emergency battery below a threshold voltage or the emergency battery powering the implantable blood pump a duration of time that exceeds a threshold time period. The method may include comparing the identified voltage of the emergency battery with a threshold voltage or comparing the identified duration of time with a threshold time period. The threshold voltage may be 10.4 volts or less for example. Thus, in some embodiments, the blood pump may be transitioned to the second operational mode from the first operational mode when the identified voltage of the emergency battery is less than 10.4 volts. The threshold duration may be 15 minutes, for example. Thus, in some embodiments, the blood pump may be transitioned to the second operational mode from the first operational mode when the emergency battery powers the pump for 15 minutes or more.

Further, methods of the present invention may include determining whether a first cable and a second cable couple one or more external power sources to the controller. This may include steps of monitoring voltage information associated with the first cable and the second cable and comparing the voltage information to a connection threshold. Thereafter, the first and/or second cable may be determined to be connected when the associated voltage information is greater than or equal to the connection threshold. The first or second cable may be determined to be disconnected when the associated voltage information is less than the connection threshold. If it is determined that the cable is disconnected from the controller, a disconnect fault status may be reported to the first or second cable in some embodiments.

In some embodiments, the signal to the blood pump to transition the blood pump from the first operational mode to the second operational mode may be transmitted when the first and second cable are determined to be disconnected from the controller for a time period greater than a threshold time period, (e.g., more than 5 minutes, 10 minutes, or 15 minutes). When the first or second cable are determined to be connected to the controller, the method may include determining whether the connected power source is an external battery or a power module based on relative state of charge information associated with the first and/or second cable.

The methods may include determining that the external power source is a rechargeable battery when the relative state of charge information associated with the first and/or second cable is greater than a minimum battery threshold and less than or equal to a maximum battery threshold. For example, a minimum battery threshold may be 330 mV and the maximum battery threshold may be 4600 mV. The relative state of charge information falling within the range may be indicative of a rechargeable lithium ion battery in some embodiments.

In some embodiments, the external power source may be determined to be a power module when the relative state of charge information associated with the first and/or second cable is greater than a power module threshold. The power module threshold may be 9800 mV, for example.

The method may further include classifying/categorizing the external power source as an unknown power source when the relative state of charge information associated with the first and/or second cable falls outside relative state of charge ranges associated with the external battery and the power module. The method may further include reporting an unknown fault status to the first and/or second cable when the external power source is categorized as an unknown power source.

In some embodiments, the operating condition associated with the blood pump power source that is indicative of a need to conserve power may be identified by monitoring relative state of charge information and the voltage information associated with the first and second cables. Fault statuses associated with the first and/or second cable may be reported based on the relative state of charge information and the voltage information. Fault statutes may be reported by: (1) reporting a first fault status (e.g., a red fault status) to the first and/or second cable when a relative state of charge is less than 1130 mV and greater than or equal to 330 mV; (2) reporting the first fault status (or red fault status) to the first and/or second cable when (a) the external power source is characterized as the rechargeable battery and the voltage is greater than 1000 mV and less than or equal to 13200 mV or when (b) the external power source is characterized as the power module and the voltage is greater than 1000 mV and less than 10400 mV; (3) reporting a second fault status (e.g., a yellow fault status less severe than a red fault status) to the first and/or second cable when the relative state of charge is less than 1930 mV and greater than or equal to 1130 mV; and (4) reporting the second fault status (or yellow fault status) to the first and/or second cable when the external power source is characterized as the power module and the voltage is greater than 10400 mV and less than or equal to 11200 mV; (5) reporting a third status (e.g., a green status or no fault status) to the first and/or second cable when the first and/or second cable is not issued the first fault status, the second fault status, the unknown fault status, or the disconnected fault status.

In some embodiments, the signal to the blood pump to transition the blood pump from the first operational mode to the second operational mode may be transmitted when the pump is operated for an extended period of time in a low power hazard condition. The low power hazard condition may be triggered when the first cable is assigned the first fault status (e.g., red), the second fault status (e.g., yellow), or the unknown fault status while the second cable is assigned the first fault status (red), unknown fault status, or the disconnected fault status. In some embodiments, the signal may be transmitted after the pump operates in such a low power hazard condition for greater than 5 minutes, for greater than 10 minutes, or greater than 15 minutes for example.

Some methods may include transmitting a second signal to the blood pump to transition the blood pump back to the first operational mode when the first cable or second cable is assigned the third status (e.g., green or no fault status) or when the first cable and the second cable are assigned the second fault status (e.g., yellow status).

In some embodiments, the first operational mode may be a pulsatile operational mode and the second operational mode may be a constant speed operational mode. Optionally, the first operational mode and the second operational mode may both be pulsatile operational modes. The second operational mode may consume less power than the first operational mode by operating at a lower flow rate. In some embodiments, the first operational mode and the second operational mode may be a constant speed modes. The second operational mode may consume less power than the first operational mode by operating at a lower flow rate.

In further embodiments an implantable blood pump system is provided. The system may include an implantable blood pump configured to supplement or replace a pumping function of a heart. The system may further include a controller coupled with the implantable blood pump. The controller may be configured to categorize or classify one or more power sources that are powering the implantable blood pump. The controller may further be configured to identify an operating condition associate with the one or more classified power sources that is indicative of a need to conserve power. The controller may also be configured to transmit a signal to the blood pump to transition between a first operational mode and a second operational mode when upon the identification of the power source status that is indicative of the need to conserve power. The second operational mode may be configured to consume less power than the first operational mode.

In some embodiments, the first operational mode may be a pulsatile pumping operation and the second operational mode may be a constant speed operation. The constant speed operation may be configured to consume less power than the pulsatile pumping operation. Alternatively, the first operational mode may comprise a first pulsatile pumping mode and the second operational mode may comprise a second pulsatile pumping mode. The second pulsatile pumping mode may consume less power than the first pulsatile pumping mode. In some embodiments, the first operational mode may comprise a first constant speed mode and the second operational mode may comprise a second constant speed mode—the second constant speed mode may consume less power than the first constant speed mode.

In some embodiments the controller may be configured determine or categorize one or more power sources coupled with the blood pump. The controller may monitor the associated power source based in-part on how the controller categories the operative power source. The controller may be configured to determine when to transition to the second operational mode based on the monitoring of the one or more power sources.

In some embodiments, the controller may be configured to couple to one or more external power sources for powering the blood pump. The controller may further include an emergency battery for powering the blood pump when the controller is disconnected from the external power source. The controller may be configured to transmit the signal to transition the blood pump from the first operational mode to the second operational mode when the controller determines that the emergency battery is powering the blood pump for greater than a threshold duration of time. The threshold duration of time may be greater than 5 minutes in some embodiments, (e.g., 10 minutes, 15 minutes, or the like).

The controller may also be configured to couple to one or more external power sources for powering the blood pump and while also including an emergency battery for powering the blood pump when the controller is disconnected from the external power source. The controller may transmit signals to the blood pump to transition from the first operational mode to the second operational mode when the power monitor determines that the emergency battery is below a threshold voltage. The threshold voltage may be less than 12.0 volts in some embodiments, (e.g., 11.0 volts, 10.4 volts, or the like).

In some embodiments, the controller may be configured to couple to one or more external power sources by a first cable and a second cable. The controller may be configured to classify the one or more power source or determine the power sources coupled thereto. In some embodiments, the controller includes a power monitor module that may be configured to classify/describe the one or more coupled power sources and to monitor the operational status of the power source based on the categorizations of the power source. In some embodiments, the controller may be configured to monitor the status of the power source based on voltage information and relative state of charge information associated with the first cable and the second cable. In some embodiments a system may include an analog to digital driver unit configured to gather voltage information and relative state of charge information associated with the first cable and the second cable.

The controller may be configured to report disconnect fault statuses to the first and/or second cable when voltage information associated with the first and/or second cable is below a connection threshold. In some embodiments, the controller may be configured to characterize the power source as a battery, a power module, or an unknown power source, and to report unknown fault statuses to the associated first and/or second cable when the relative state of charge information is indicative of an unknown power source.

The controller may further be configured to monitor the status of the battery or the power module by issuing fault statuses to the first and/or second cable depending on relative state of charge information and voltage information associated with the first and/or second cable. A controller may be configure to trigger or indicate a low power hazard condition based on the fault statuses issued to the first and/or second cable.

Optionally, the controller may be configured to transmit the signal to the blood pump to transition from the first operational mode to the second operational mode when the system operates with low power hazard condition and/or detects disconnection of the external power source from the controller for greater than a threshold duration of time. In some embodiments, the threshold duration of time may be a time period greater than 5 minutes or greater than 10 minutes, for example. In some embodiments, the controller may transmit the signal after operating with a low power hazard condition and/or disconnected condition for 15 minutes or more.

The details of one or more implementations are set forth in the accompanying drawings and the description below. Other features will be apparent from the description and drawings, and from the claims.

BRIEF DESCRIPTION OF THE DRAWINGS

FIG. 14 illustrates a chart describing exemplary alarms for various situations depending on the status of a first cable (e.g., black cable status) and a second cable (e.g., white cable status) according to embodiments of the present invention.

DETAILED DESCRIPTION OF THE INVENTION

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

Figure 1:
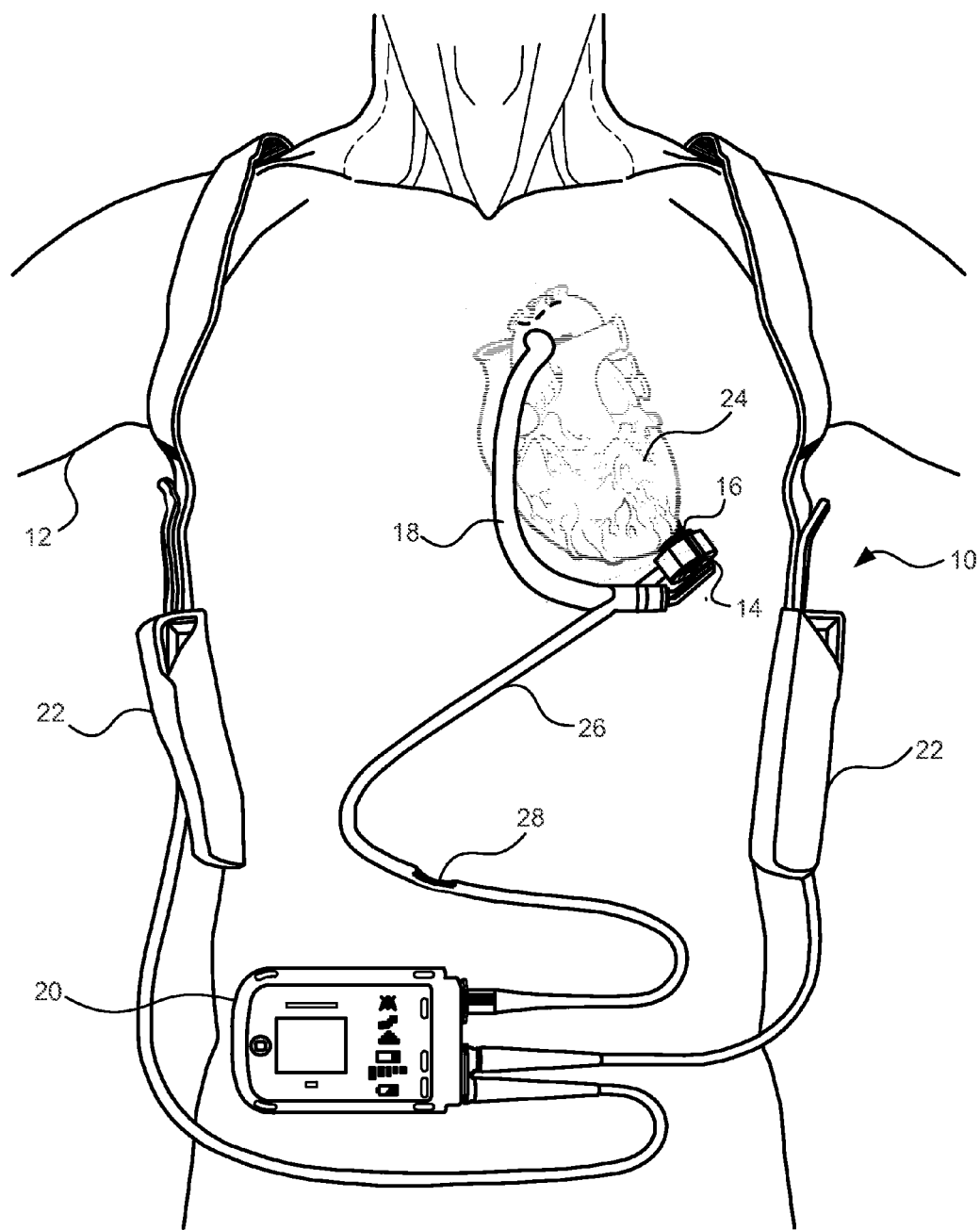
FIG. 1 is an illustration of a mechanical circulatory support system implanted in a patient's body.
Figure 2:
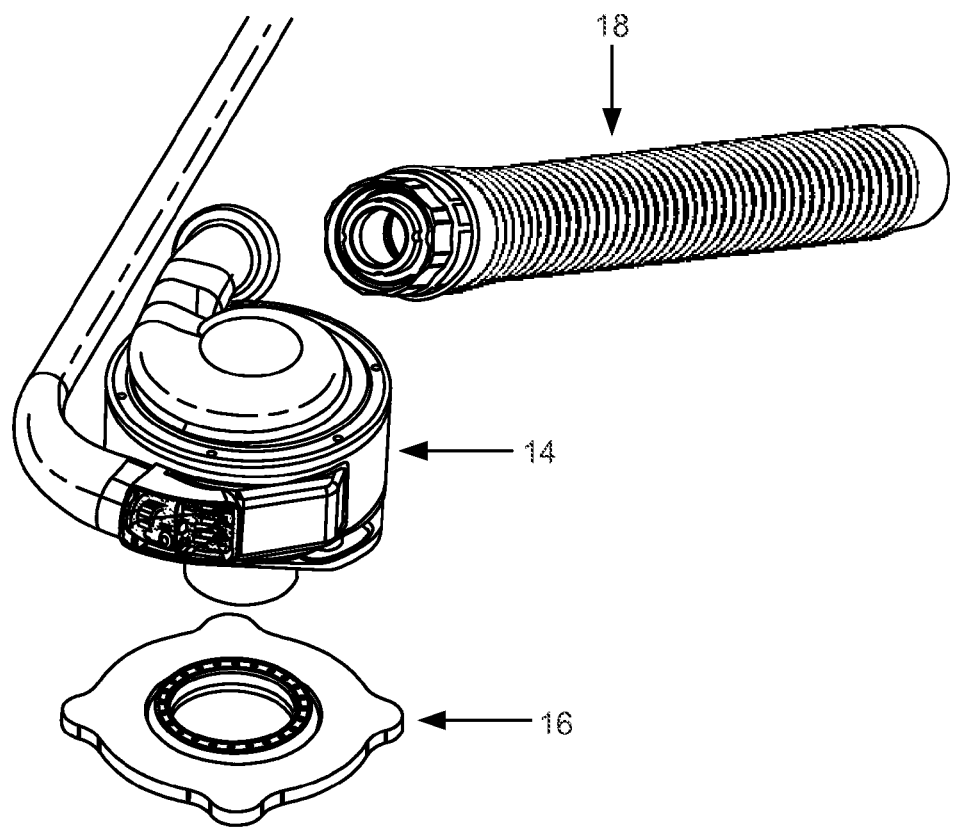
FIG. 2 is an exploded view of certain components of the circulatory support system that are implanted in a patient's body.

FIG. 1 is an illustration of a mechanical circulatory support system 10 implanted in a patient's body 12. The mechanical circulatory support system 10 comprises a implantable blood pump 14, ventricular cuff 16, outflow cannula 18, system controller 20, and power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 which exits through the patient's abdomen 28, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. Examples of such modifications are further described in U.S. Pat. No. 8,562,508 and U.S. Patent Publication No. 2013/0127253, all of which are incorporated herein by reference for all purposes in their entirety.

Figure 3:
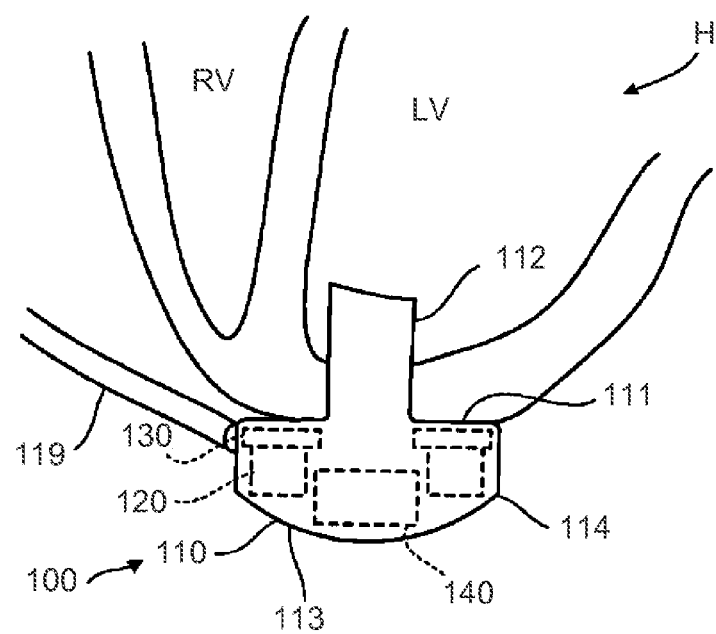
FIG. 3 is an illustration of a blood pump in an operational position implanted in a patient's body.
Figure 4:
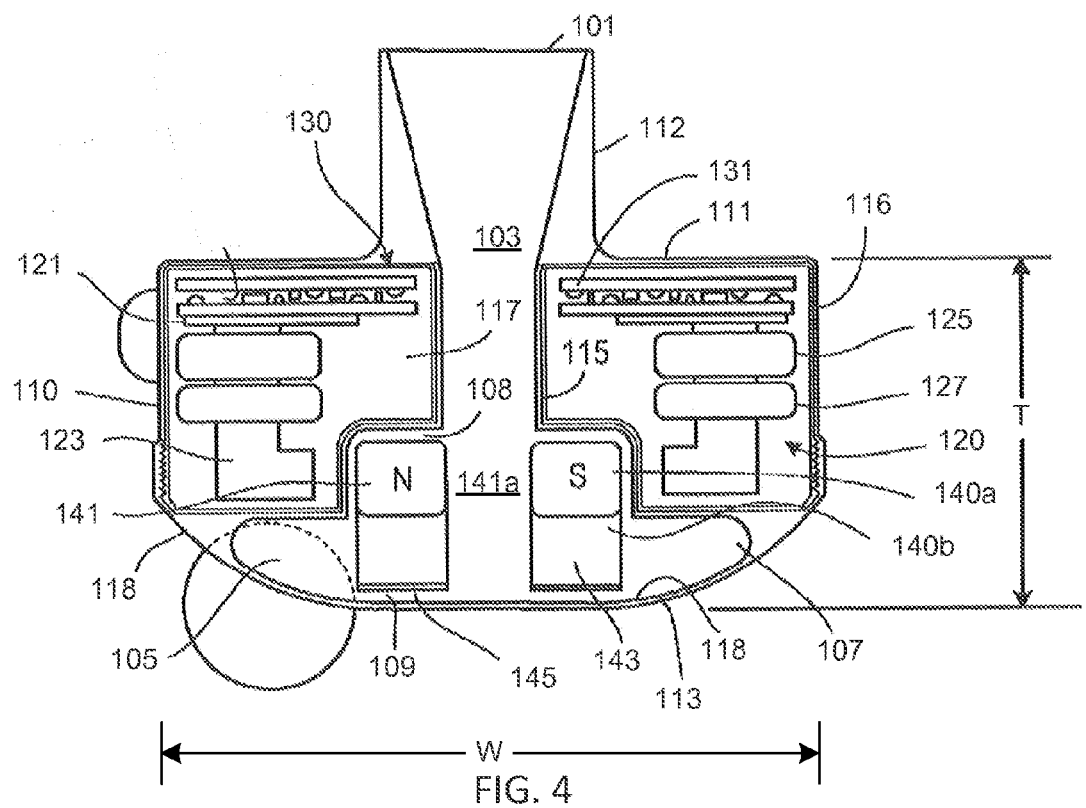
FIG. 4 is a cross-sectional view of the blood pump of FIG. 3.
Figure 5:
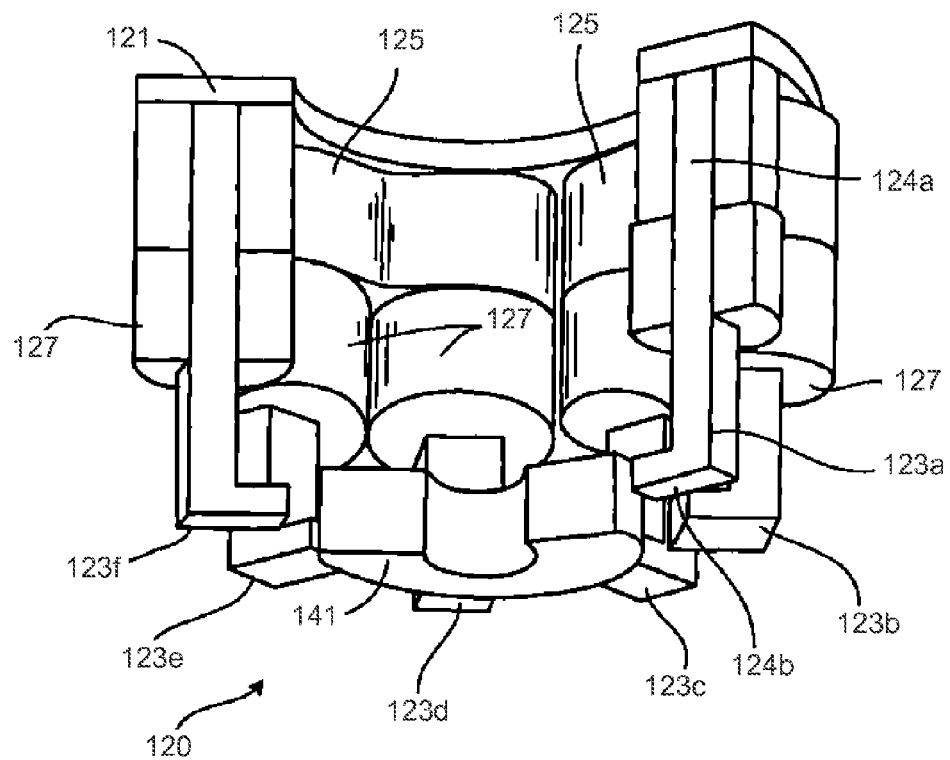
FIG. 5 is a partial cut-away perspective view of a stator of a blood pump.

With reference to FIGS. 3 to 5, a left ventricular assist blood pump 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118.

The blood exits the volute 107 through the outlet opening 105, which may be coupled to an outflow cannula.

Figure 6:
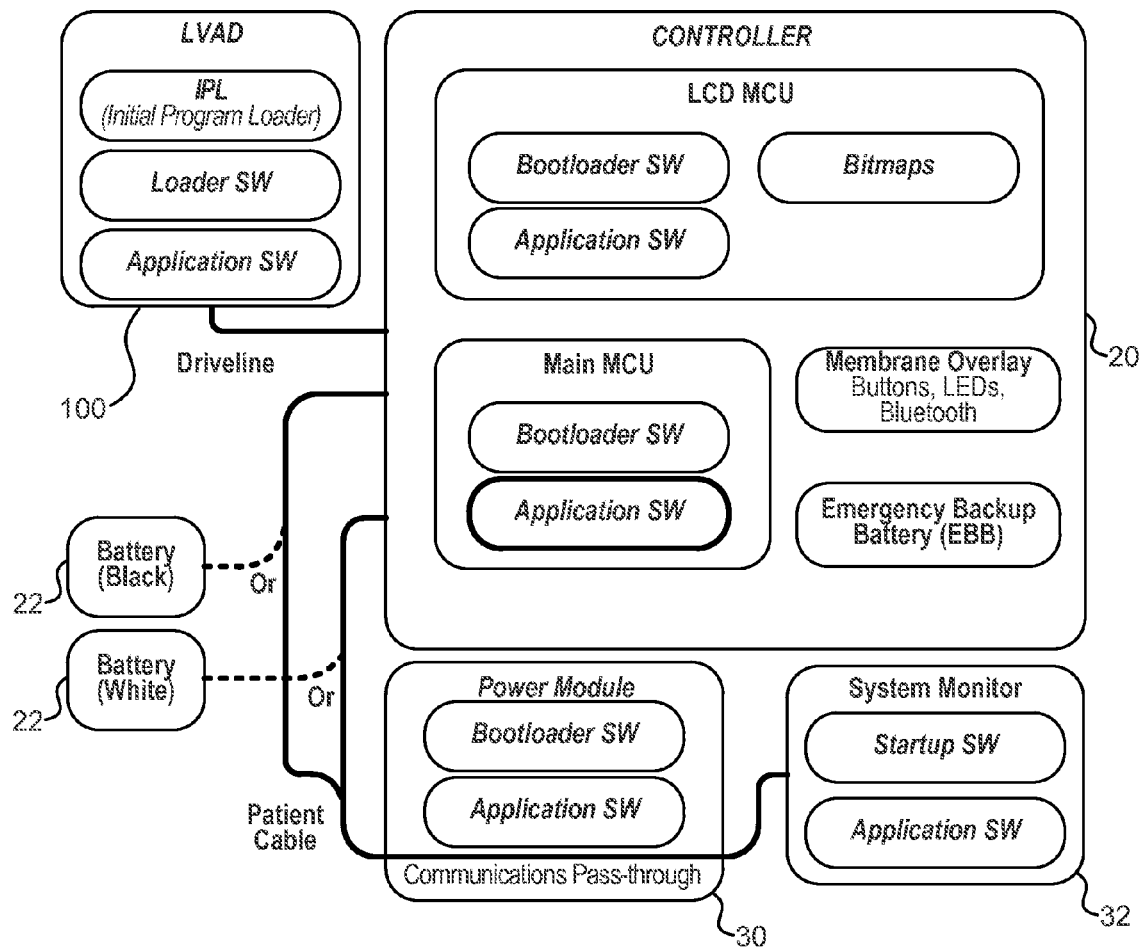
FIG. 6 is a schematic diagram of an overall communication architecture of the mechanical support system of FIG. 1.

FIG. 6 is a schematic diagram of an overall communication architecture of the mechanical support system of FIG. 1. A driveline couples the implanted blood pump 100 to the system controller 20, which monitors system operation via various software applications. The blood pump 100 itself also includes several software applications that are executable by the on board electronics 130 (e.g., processors) for various functions, such as to control radial levitation and/or drive of the rotor of the pump 100 during operation. The system controller 20 may in turn be coupled to batteries 22 or a power module 30 that connect to an AC electrical outlet. The system controller 20 may also include an emergency backup battery (EBB) to power the system (e.g., when the batteries 22 are depleted) and a membrane overlay, including Bluetooth capabilities for wireless data communication. An external computer having a system monitor 32 that is configurable by an operator, such as clinician or patient, may further be coupled to the circulatory support system for configuring the system controller 20, implanted blood pump 100, and/or patient parameters, updating software on the system controller 20 and/or implanted blood pump 100, monitoring system operation, and/or as a conduit for system inputs or outputs.

In addition to producing blood flow at a desired rate, a pulsatile blood flow pattern may be desired. A pulsatile blood flow pattern includes time periods of relatively high blood flow rates and blood pressures and time periods of relatively low blood flow rates and blood pressures. Such a pulsatile blood flow pattern may be desired to augment or replace a weakened pulse in patients, especially those whose native cardiac output is small compared to the volume flow rate of the blood pump. Additionally, a pulsatile blood flow pattern may be desired to produce a physiologic response similar to that of a native pulsatile blood flow pattern and/or blood pulse pressure from a healthy heart. This physiologic response may be markedly different than the response of a blood pump operating at a constant speed. While non-pulsatile circulation can lead to certain physiologic, metabolic, and vasomotor changes, the clinical relevance of pulsatility for VADs is unclear. Nevertheless, it is hypothesized that pulsatile circulation may reduce blood stasis in the ventricles, help exercise the aortic valve, improve washing on the distal side of atherosclerotic lesions, increase coronary and/or end organ perfusion, reduce the risk of ventricular suction, reduce the propensity for maladies related to reduced pulsatility, such as arteriovenous malformations, and increase myocardial recovery. Further, it is expected that these phenomena do not require mimicking a native pulse waveform in its entirety. Rather, such may be accomplished with the techniques and waveforms described herein.

Importantly, various characteristics of the artificial pulse may differ substantially from those of a physiologic pulse even while producing a response in the body that is similar to that caused by the physiologic pulse. Although with the multitude of potential clinical advantages there may be different aspects of a native pulse that mediate physiologic response, it is generally understood that the dominant source of dissipated energy that characterizes a meaningful pulse is the pressure wave generated at the start of cardiac systole. Accordingly, the artificial pulse described herein can include a relatively brief perturbation of a nature designed to produce such dissipated energy.

In some implementations, an artificial pulse cycle includes a perturbation period that simulates the pulse pressure that occurs at the leading edge of systole of a physiologic pulse. The perturbation period can include, for example, a period during which the blood pump 100 is operated at a low speed, followed immediately by a period during which the blood pump 100 is operated at a higher speed. The artificial pulse cycle can also include a period longer than the perturbation period during which the pump 100 is operated at an intermediate speed, for example, a speed maintained between the speeds realized during the perturbation period.

Operating the pump at the intermediate speed can contribute to a high operating efficiency. The efficiency achieved can be greater than, for example, the efficiency of a pump that only alternates between equal periods of operation at a high speed and at a low speed. Typically, a continuous flow pump operates with highest efficiency near the middle of its rotational speed range. Therefore, it can be advantageous to operate such a pump at or near a mid-range speed for at least a portion of an artificial pulse cycle.

Some of the parameters that affect physiologic phenomena include pulse pressure and the rate of blood pressure change (dp/dt). For the blood pump 100, for example, pulse pressure and time variation in blood pressure are affected by the angular velocity of the rotor 140. Thus, the blood pump 100 can be selectively controlled to produce a pulsatile blood flow pattern, including a desired pulse pressure and/or a desired rate of pressure change, by producing a pump speed pattern that includes a time period of relatively high rotor rotation speeds and a time period of relatively low rotor rotation speeds. In some implementations, the pulse pressure produced by the blood pump 100 or produced by the blood pump 100 and the patient's heart H in combination can be approximately 10 mmHg or more, such as from approximately 20 mmHg to approximately 40 mmHg.

Figure 7:
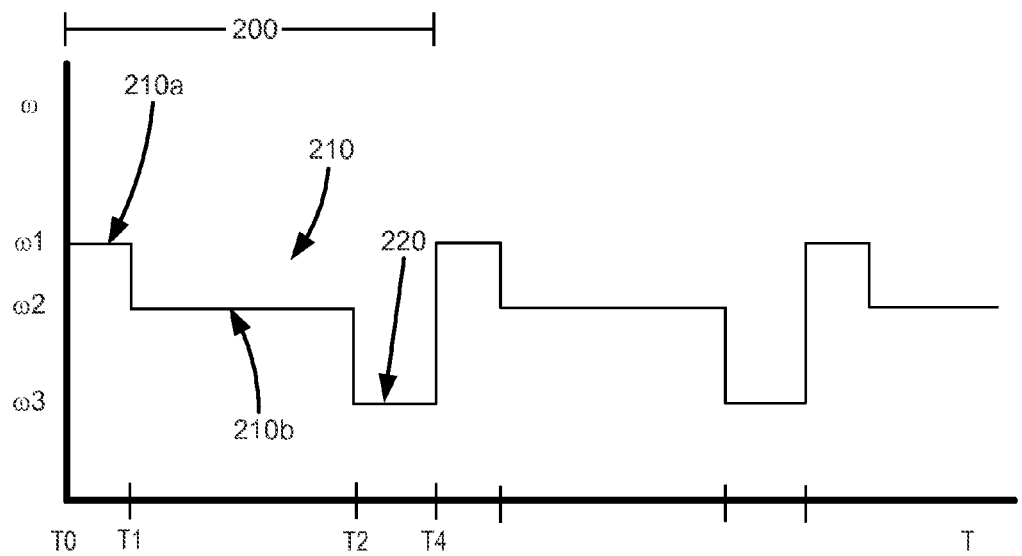
FIGS. 7-10 are diagrams illustrating pump speed patterns.

For example, the blood pump 100 can be operated to produce a pump speed pattern 200, illustrated in FIG. 7. The pump speed pattern 200 includes a first portion 210 with high pump speed producing a relatively high blood pressure, and a second portion 220 with low pump speed producing a relatively low blood pressure. Additionally, the pulsatile blood flow pattern can include a transition between the first portion 210 and the second portion 220 that produces a desired rate of pressure change in the patient's circulatory system, such as a rate of pressure change that simulates a natural physiologic pulse and that produces desired physiological effects associated with rate of pressure change. In some implementations, the rate of pressure change produced by the transition is, for example, between 500 to 1000 mmHg per second.

The first portion 210 and/or the second portion 220 of the pump speed pattern 200 can include multiple segments. In some implementations, the segments each have predetermined durations. As also shown in FIG. 7, the first high speed portion 210 of the pump speed pattern 200 includes a first segment 210a and a second segment 210b. In the first segment 210a, the rotor 140 is rotated at a first rotation speed $\omega 1$ for a first period of time from a time T0 to a time T1. At the time T1, the rotation speed of the rotor 140 is rapidly decreased from the first rotation speed $\omega 1$ to a second rotation speed $\omega 2$, producing a stepped transition. The rotor 140 is rotated at the second rotation speed $\omega 2$ for a second period of time from the time T1 to a time T2 during a second segment 210b of the first portion 210 of the pump speed pattern 200. At the time T2, the rotation speed of the rotor 140 is decreased to a third rotation speed $\omega 3$ for a third period of time from the time T2 to a time T4 during the second portion 220 of the pump speed pattern 200. This speed decrease may be as rapid as the aforementioned speed increase, or more gradual to mimic pressure changes during native diastole.

In the pump speed pattern 200, the second rotation speed ω2 is a target high blood flow pump speed, and the first rotation speed ω1 is a desired overshoot pump speed that is selected to increase the rate of change of the blood pressure during the first period. The first period of time from the time T0 to the time T1, during which the blood pump 100 is operated at the first rotation speed ω1, is shorter than the second period of time from the time T1 to the time T2, during which the blood pump 100 is operated at the second rotation speed ω2. The first period of time can be from approximately 0.01 seconds to approximately 1 second. In some implementations, the first period of time is approximately 0.05 seconds in duration. In some implementations, the first period of time can be approximately equal to, or greater than the second period of time.

Additionally, the duration of the first period can be selected to produce a desired pulse pressure, i.e., the difference between blood pressure before the speed change time T1 and during the time T1, and can be selected independently of the duration of the second period of time. The first portion 210, including the first and second time periods from the time T0 to the time T2, is longer than the second portion 220. In some implementations, the first and second time periods from the time T0 to the time T2 can be shorter than, longer than, or substantially the same duration as the second portion 220. For example, to increase the duration of pumping at the higher flow rate relative to pumping at the lower rate while still benefiting from the occasional pulse, it may be advantageous for the first portion 210 to be longer than the second portion 220. If desired, the speed of the blood pump 100 is increased to the first rotation speed ω1 and the pump speed pattern 200 can be repeated. The pump speed pattern 200 can be repeated on a continuous or discontinuous basis, and the increase of rotation speed of the rotor 140 is also sufficiently rapid to produce a desired rate of pressure change.

The concept of overshooting the rotation speed ω2 with a greater speed, such as rotation speed ω1, is based upon partly decoupling pulse pressure, i.e. the difference between the blood pressures before and after the speed change, from the volume flow rate at the higher speed. Thus. target pulse pressures and volume flow rates can be attained at various flow conditions. Ideal values will vary with particular pump design and requirements.

As shown in FIG. 7, the period 210b can be longer than the period 210a. The period 21 210b can also be longer than the portion 220. In some implementations, the duration of the period 210b is more than half of the duration of the pump speed pattern 200. For example, the duration of the period 210b can be 60%, 70%, 80% or more of the duration of the pump speed pattern 200. As an alternative, depending on patient needs and pump characteristics, the duration of the period 210b can be 50% or less of the duration of the pump speed pattern 200, for example, 40%, 30%, 20% or less.

Operating the pump at the rotation speed ω2 during the period 210b can contribute to a high hydraulic efficiency during the pump speed pattern 200. During the pump speed pattern 200, the pulse pressure generated in a patient's body is generally correlated to the change in pump rotation speed, for example, the magnitude of the speed change between the speeds ω3 and ω1 at time T4. Therefore, to simulate a pressure change that occurs at the beginning of systole of a physiologic pulse, a significant speed differential between the rotation speeds ω3 and ω1 is generally desired. The speed differential can be, for example, 1000 rpm, 2000 rpm, or more depending on the characteristics of the blood pump 100. Due to the magnitude of the speed differential, one or both of the speeds ω3 to ω1 may occur outside the range of highest operating efficiency of the blood pump 100.

The rotation speed ω2 can be a speed that results in a high hydraulic efficiency of the blood pump 100, for example, a speed near the middle of the operating range of the blood pump 100. During the pump speed pattern 200, the blood pump 100 can operate at the speed ω2 that results in high efficiency for a significant portion of the pump speed pattern 200, contributing to a high efficiency. As described above, the blood pump 100 can operate at the speed ω2 for more than half of the duration at the pump speed pattern 200. Thus the blood pump 100 can operate in a highly efficient manner for the majority of the pump speed pattern 200 and can also produce a pressure change that simulates the beginning of systole of a physiologic heart. Accordingly, some implementations of the pump speed pattern 200 can provide a higher efficiency than control modes that attempt to mimic all aspects of a native cardiac cycle.

The length of the period 210b relative to the length of the pump speed pattern 200 can vary based on the frequency of the artificial pulse. The duration of the period 210a and of the portion 220, by contrast, can be independent of the pulse rate. To produce the desired physiological response, a minimum duration for the period 210a and the portion 220 can be selected, for example, 0.125 seconds. The period 210b can fill the remainder of the pump speed pattern 200.

As an example, the pump speed pattern 200 can have a duration of one second, for a frequency of 60 cycles per minute. Given that the period 210a and the portion 220 have a combined duration of 0.125 seconds, the period 210b can have a duration of 0.750 seconds, or 75% of the pump speed pattern 200. As another example, when the pump speed pattern 200 has a duration of two seconds (and thus a frequency of 30 cycles per minute), the duration of the period 210b can be 1.75 seconds, which is 87.5% of the duration of the pump speed pattern 200.

In some implementations, the rotation speed ω2 is selected such that the operation of the blood pump 100 at the rotation speed ω2 produces a flow rate that has a predetermined relationship relative to the average flow rate during the pump speed pattern 200. The flow rate during the portion 210b can be within a predefined range of the average flow rate, for example, within 30% or within 10% of the average flow rate. The flow rate during the portion 210b can be substantially equal to the average flow rate.

Selecting the rotation speed ω2 to produce a flow rate that is substantially equal to the average flow rate can facilitate a transition between a pulsatile control mode and another control mode, such as a continuous flow control mode. In some implementations, the blood pump 100 operates at a particular constant speed for the greater part of the pump speed pattern 200. Operation at the constant speed can occur during, for example, the period 210b. By adjusting the speeds ω1 and ω3 and duration of the period 210a and of the portion 220, the average pump volume flow rate can be tuned to substantially match an average pump volume flow rate that would be realized in a different optional setting. Consequently, a clinician or patient can switch from an artificial pulse mode to another control mode in a manner that causes only a small difference or no difference in average volume flow rate. This can provide a clinical advantage when the artificial pulse is a selectable option among at least one alternative, for example, a constant speed option.

As an example, a speed set by a clinician for a constant speed mode can also be utilized for a constant speed portion of an artificial pulse mode. The speed can be selected by the clinician to produce a desired volume flow rate through the blood pump 100 during the constant speed mode (e.g., during continuous flow or non-pulsatile operation of the blood pump 100). In the artificial pulse mode, the same selected speed can be used as, for example, the rotation speed ω2 during the period 210b of the pump speed pattern 200. The speeds ω1, ω3 and the duration of the period 210a and the portion 220 are calculated or chosen to approximately balance the volume flow rate for the pump speed pattern 200. For example, the reduced flow rate during the portion 220 can offset the increased flow rate during the portion 210a. As a result, the net volume flow rate during the pump speed pattern 200 can substantially match the volume flow rate during the constant speed mode. Thus in either the constant speed mode or the artificial pulse mode, the volume flow rate can be approximately the same, permitting the clinician to switch from one mode to another without affecting the volume flow rate. This can help avoid potentially dangerous conditions that could occur if switching from one mode to another resulted in sudden changes in flow rate. for example, a sudden decrease in volume flow rate could cause acutely insufficient perfusion for the patient, and a sudden increase in volume flow rate could cause ventricular suction and arrhythmia.

Figure 8:
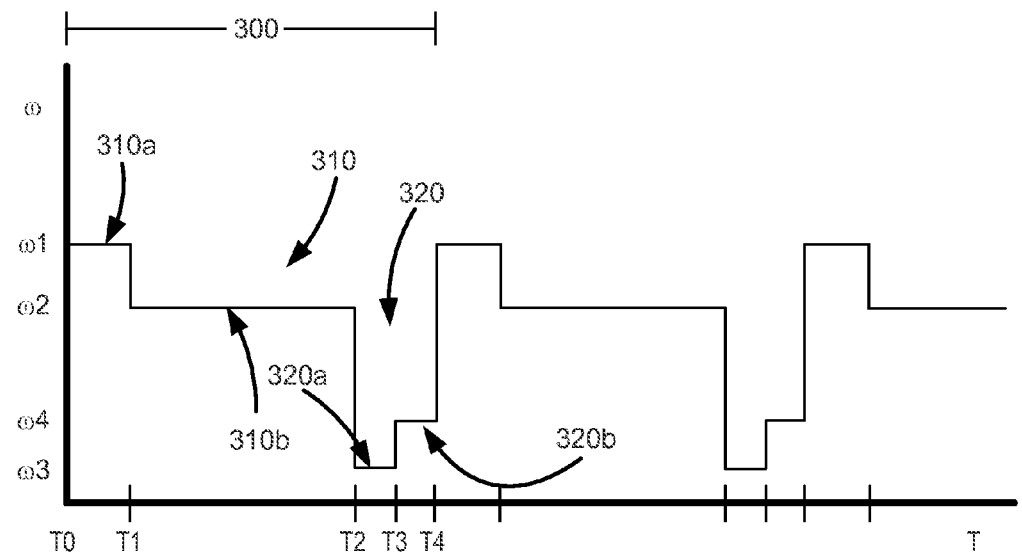

As mentioned above, the second portion 210 of the pump speed pattern 200 can also include multiple segments. For example, as shown in FIG. 8, a pump speed pattern 300 includes a first portion 310 that has a first segment 310a and a second segment 310b and the pump speed pattern 300 includes a second portion 320 that has a first segment 320a and a second segment 320b. During the first segment 310a, from the time T0 to the time T1, the blood pump 100 is operated at the first rotation speed ω1. At the time T1, the speed of the blood pump 100 is reduced to the second rotation speed ω2, and the blood pump 100 is operated at the second rotation speed ω2 for the second period of time from the time T1 to the time T2. At the time T2, the speed of the blood pump 100 is reduced from the second speed ω2 to the third rotation speed ω3. The blood pump 100 is operated at the third rotation speed ω3 for a third period of time from the time T2 to a time T3 during a first segment 320a of the second portion 320 of the pump speed pattern 300. At the time T3, the speed of the blood pump 100 is increased from the third rotation speed ω3 to a fourth rotation speed ω4, and the blood pump 100 is operated at the fourth rotation speed ω4 during a fourth period of time from the time T3 to the time T4 during a second segment 320b of the second portion 320 of the pump speed pattern 300. If desired, the speed of the blood pump 100 is increased to the first rotation speed ω1 and the pump speed pattern 300 can be repeated. The pump speed pattern 300 can be repeated on a continuous or discontinuous basis, and the increase of rotation speed of the rotor 140 is also sufficiently rapid to produce a desired rate of pressure change.

Similar to the concept of overshooting ω2 in pattern 200, the concept of overshooting the rotation speed ω4 with a lower rotation speed, such as the rotation speed ω3, is also based upon decoupling pulse pressure from the volume flow rate at the lower rotation speed ω4. Thus, the pump speed pattern 300 more completely decouples target pulse pressures and volume flow rates than the pump speed pattern 200, and ideal values can be attained, or more closely approximated, at various flow conditions.

Figure 9:
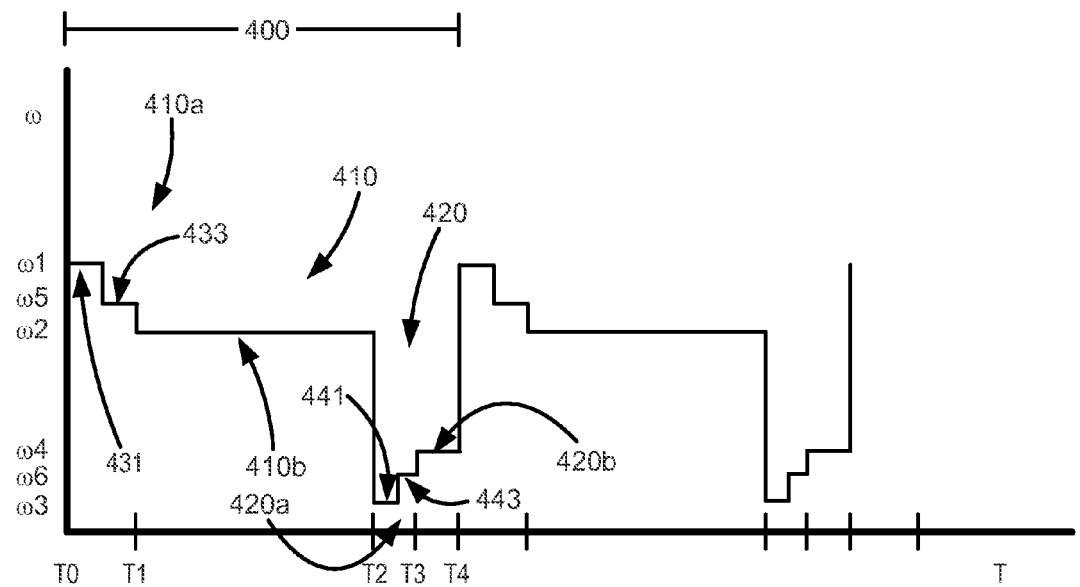

While a single overshoot pump speed for a transition between pump speeds are illustrated and described with reference to FIGS. 7 and 8, multiple overshoot pump speeds for one or more transitions can be used. For example, FIG. 9 illustrates a pump speed pattern 400 that includes multiple overshoot pump speeds for each transition. The pump speed pattern 400 includes a first portion 410 having a first segment 410a and a second segment 410b, and that includes a second portion 420 having a first segment 420a and a second segment 420h. The first segment 410a of the first portion 410 of the pump speed pattern 400 includes a first step 431 during which the blood pump 100 is operated at the first rotation speed ω1 to overshoot the target pump speed ω2 and a second transition step 433 during which time the blood pump 100 is operated at a fifth speed ω5 to transition from the first rotation speed ω1 to the second rotation speed ω2. Similarly, the first segment 420a of the second portion 420 includes a first step 441 during which the blood pump 100 is operated at the third rotation speed ω3 and a second segment 443 during which the blood pump 100 is operated at a sixth speed ω6 to transition between the third speed ω3 and the fourth rotation speed ω4. If desired, the speed of the blood pump 100 is increased to the first rotation speed ω1 and the pump speed pattern 400 can be repeated. The pump speed pattern 400 can be repeated on a continuous or discontinuous basis, and the increase of rotation speed of the rotor 140 is also sufficiently rapid to produce a desired rate of pressure change.

The concept of creating multiple stepwise rotation speed changes is based upon producing the physiologic response that is similar to that produced during human cardiac systole and diastole. This is distinct from mimicking the nature of a native pulse waveform in its entirety. As described above, greater hydraulic efficiency can often be achieved by avoiding imitation of the physiologic pressure waveform over the pulse cycle. It was previously mentioned that an artificial pulse offers a multitude of potential clinical advantages. For some or all of these potential clinical advantages, the benefit of closely matching the energy dissipated during a healthy native pulse varies. To the extent that close matching facilitates achieving these potential clinical advantages, the additional complexity of pattern 400 may be warranted.

Figure 10:
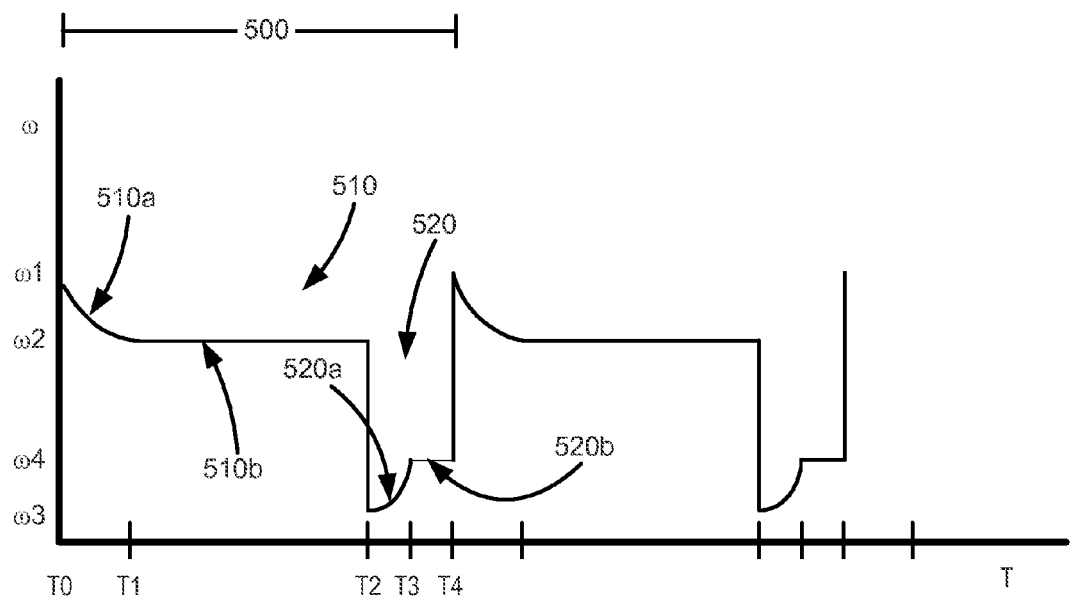

In contrast to the stepped or discontinuous transitions discussed above with respect to FIGS. 7-9, smooth or continuous transitions may be used in place of, or in combination with, stepped transitions between different pump operation speeds. For example, smooth transitions are illustrated in the pump speed pattern 500 of FIG. 10. The pump speed pattern 500 includes a first portion 510 and a second portion 520. The first portion 510 includes a first segment 510a during which the speed of the pump 100 is decreased gradually, at a strategically-selected rate, from the first rotation speed ω1 to the second rotation speed ω2 from the time T0 to the time T1. The selected rate of pump speed decrease can be, for example, a particular linear rate or a particular non-linear rate. During the second segment 510b of the first portion 510, from the time T1 to the rime T2, the blood pump 100 is operated at the second rotation speed ω2. Similarly, the second portion 520 includes a first segment 520a during which the speed of the blood pump 100 is increased gradually, at a strategically-selected rate, from the third rotation speed ω3 to the fourth rotation speed ω4 from the time T2 to the time T3. During the second segment 520b of the second portion 520, from the time T3 to the time T4, the blood pump 100 is operated at the fourth rotation speed ω4. If desired, at time T4, there is a step increase in the rotation speed of the rotor 140 can be rapidly increased to the first rotation speed ω1, and the pump speed pattern 500 is repeated.

The concept of creating multiple speed changes at a strategically-selected rate is based upon producing the physiologic response that is similar to that produced during human cardiac systole and diastole. For example, if very accurate matching of energy dissipation during a human pulse is necessary, the additional complexity of pattern 500 may be warranted.

The pump speed pattern 500 illustrates the difference between stepped transitions discussed above with respect to pump speed patterns 200-400, produced by rapidly changing the rotation speed of the rotor 140, and the gradual transitions of the first segment 510a of the first portion 510 and the first segment 520a of the second portion 520 of the pump speed pattern 500. Such gradual transitions can be included, for example, to mimic pressure changes exhibited during native diastole, as may be achieved by the gradual transition of the first segment 510a of the first portion 510 of the pump speed pattern 500. In some implementations, one or more of the rotation speed decreases of a pump speed pattern can be gradual transitions. For example, a pump speed pattern can include a gradual decrease in rotation speed from the first rotation speed ml to the third rotation speed ω3 and a stepped transition from the third pump speed ω3 back to the first rotation speed ω1. Various combinations of stepped and gradual transitions can be included in a pump speed pattern to produce a desired arterial pressure wave form, or other desired physiologic effect. Additionally, the type of transition between rotation speeds can affect power consumption of the blood pump 100, and the pump speed pattern can be selected based, at least in part, on power consumption considerations.

For all the pump speed patterns discussed it should be appreciated that although rotor speed is the technological parameter utilized to impart an artificial pulse, any physiologic effect is related to the consequential pressure and flow patterns, including pulse pressure, the maximum time variation in rate of blood pressure change (dp/dt), and the like. Rotor speed is not intrinsically physiologically meaningful. The human vascular system naturally dampens the native pulse produced by the heart, and it will do the same for an artificial pulse produced as described. The invention describes a utilitarian combination of factors that result in a physiological meaningful pulse. Thus, the pump speed patterns 200-500 described above are exemplary combinations of parameters that result in a physiologically meaningful pulse.

Figure 11:
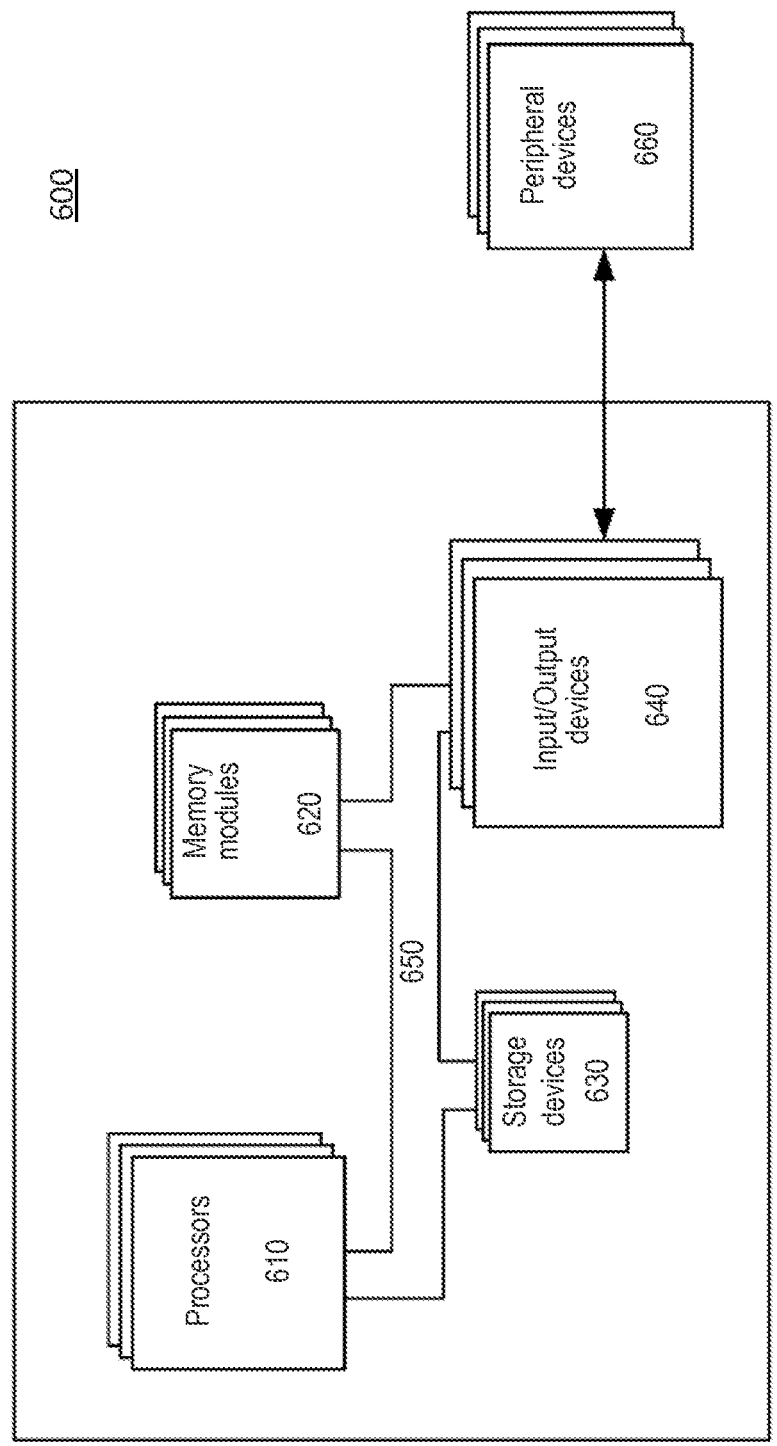
FIG. 11 is a diagram of a computer system.

In use, the pump speed patterns 200-500 can be generated by a controller that is configured to generate an electrical drive signal to operate the blood pump 100. For example, the controller can include a computer system 600, shown in FIG. 11, that outputs an electrical current to operate the blood pump 100. In order to produce the pump speed pattern 200 described above, the controller outputs a first electrical current from the time T0 to the time T1. At the time T1, the controller reduces the output electrical current to a second current that is lower than the first electrical current, and outputs the second electrical current from the time T1 to the time T2. At the time T2, the controller reduces the output electrical current from the second current to a third current, and outputs the third electrical current from the time T2 to the time T4.

The computer system 600 includes one or more processors 610, memory modules 620, storage devices 630, and input/output devices 640 connected by a system bus 650. The input/output devices 640 are operable to communicate signals to, and/or receive signals from, one or more peripheral devices 660. For example, a peripheral device 660 can be used to store computer executable instructions on the memory modules 620 and/or the storage devices 630 that are operable, when executed by the processors to cause the controller to generate a waveform to control the operation of the pump 100 and produce a pump speed pattern, such as the pump speed patterns 200-500.

Additionally, the controller can include a sensor that provides a signal that indicates activity of the heart H. For example, the controller can include a sensor that provides a signal indicative of power consumption of the blood pump 100. The signal can be used to determine when the left ventricle LV contracts. For example, the power consumption of the blood pump 100 may, for a given operating speed, increase as the left ventricle LV contracts. Based on the determined heart activity, the controller can adjust the generated control waveform. For example, the controller can automatically adjust the timing and duration of the first portion 210 and the second portion 220 of the pump speed pattern 200 such that the first portion 210 approximately coincides with a contraction of the left ventricle LV. The pump 100 is controlled such that the time T0 approximately coincides with a beginning of a contraction of the left ventricle LV and the time T2 approximately coincides with an end of the contraction of the left ventricle LV. The time T4 approximately coincides with a beginning of a subsequent contraction of the left ventricle LV. Thus, the durations of the various portions and/or segments of the pump speed patterns described above can be changed individually or collectively for one or more repetitions of the pump speed patterns. Using these techniques, the controller can synchronize the pulsatile operation of the blood pump 100 with the natural physiologic pulse of the heart H.

Alternatively, the controller can generate the control waveform independently of the activity of the heart H and/or to operate in opposition to the activity of the heart H, such as where the first portion 210 occurs during left ventricular relaxation. Similarly, the controller can generate a control waveform that includes a distinctly non-physiologic pulse rate, such as fewer than 40 high-pressure periods per minute, and the waveform can be generated independently of native heart function. In some examples, the blood pump 100 can be operated to produce distinctly physiologic pulse rates, such as between 50 and 110 high-pressure periods per minute, and can be controlled dependently or independently of heart function.

A number of implementations have been described. Nevertheless, it will be understood that various modifications may be made without departing from the spirit and scope of the claimed invention. For example, the pump speed patterns described above can be used with various types of blood pumps, including axial flow blood pumps and centrifugal flow blood pumps. Similarly, the rotors of blood pumps used to produce pulsatile blood flow patterns as described above may be electromagnetically-suspended, hydraulically-suspended, mechanically-suspended, or combinations thereof. The rotors may also partially be passively magnetically-suspended. However, the effect of an artificial pulse may most accurately be simulated by a pump in which the rotor is electromagnetically suspended, with or without partial passive magnetic suspension, because in general, other things being equal, electromagnetic suspension yields a high degree of responsiveness of the rotor to speed change inputs. For example, mechanical hearings associated with mechanical suspension and/or very narrow rotor clearance gaps associated with hydraulic suspension hinder rapid acceleration of the rotor compared to similar pumps that employ electromagnetic suspension. Additionally, while the pump speed patterns described above have been described with regard to a measure of angular velocity, the pump speed patterns can be produced with regard to one or more different measures of pump speeds. Additionally, there may be a delay between a change in drive signal generated by the controller and a change in operating speed of the blood pump. Thus, the controller can be operated such that changes in the output drive signal are effected at a time to produce a corresponding change in pump operating speed at a desired time, such as a time that approximately coincides with selected activity of the heart.

In some implementations, the pump speed patterns 200-500 can include additional portions or segments during which the blood pump is operated at other speeds. For example, at desired times, the blood pump can be operated to produce a pump speed pattern that produces a desired physiologic effect, such as opening or closing the aortic valve. Such operation of the blood pump can interrupt a generally continuous repetition of a selected one or more of the pump speed patterns described above, or others, including an indefinite period of constant speed, and a selected pump speed pattern can be resumed after the desired physiologic effect has been produced. The pump speed patterns 200-500 can also include different portions or segments. For example, the second segment 210b of the first portion 210 of the pump speed pattern 200 can include multiple pump speeds. Similarly, the transitions between pump speeds, such as the reduction in pump speed from the first rotation speed $\omega 1$ to the second rotation speed $\omega 2$, can include constant, variable, exponential, combinations thereof, or other rate of speed change over time such that the transition, such as the first segment 510a of the first portion 510 of the pump speed pattern 500, is linear, curvilinear, parabolic, logarithmic, sinusoidal, stepped, or combinations thereof.

In some implementations, one or more of the pump speed changes in the pump speed patterns 200-500 can be monotonic. A transition from one speed to another may occur gradually over a period of time, yet change directly from one speed to another. For example, to decrease a pump speed from a first rotational speed to a second rotational speed, the controller can reduce the pump speed without causing an intervening period of increasing pump speed. Similarly, the transition from the first rotational speed to the second rotational speed can occur without operating the pump above the first rotational speed during the transition.

Additionally, a blood pump can be operated according to a pump speed pattern that is selected according to a pump power consumption rate associated with the pump speed pattern, a pump efficiency associated with the pump speed pattern, a blood flow rate associated with the pump speed pattern, and/or a rate of blood pressure change associated with the pump speed pattern. For example, in a first mode, the controller can be operated to produce a pump speed pattern that produces a desired rate of blood pressure change. When a low power condition is detected, the controller can be switched to a power-saving mode to produce a pump speed pattern that has a low power consumption rate, even if the desired rate of pressure change is not produced in the power-saving mode.

Figure 12:
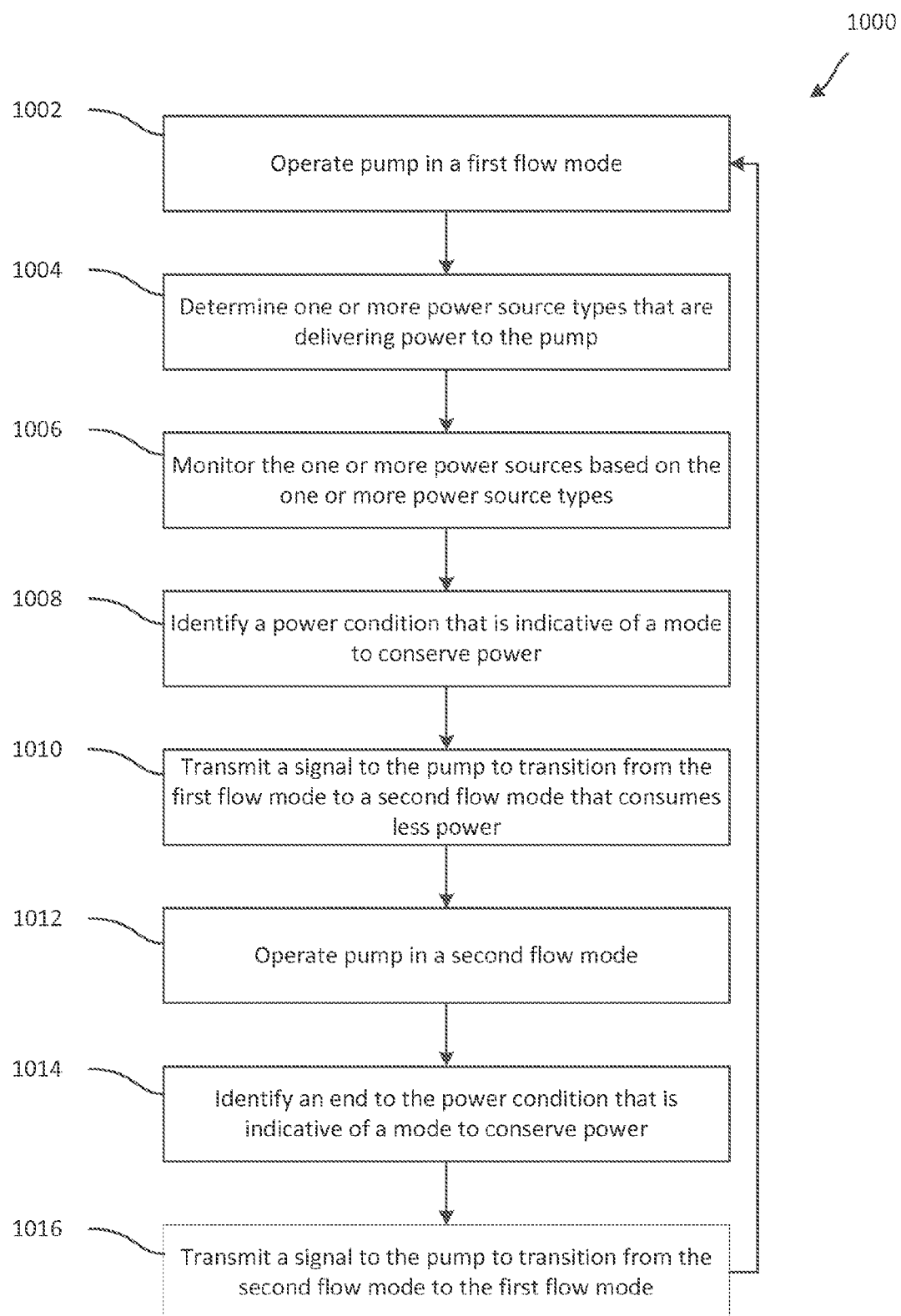
FIG. 12 illustrates an exemplary method for conserving power according to some embodiments.

FIG. 12 illustrates an exemplary method 1000 for conserving power according to some embodiments of the present invention. Method 1000 may start at step 1002 where the implantable blood pump is operated in a first flow mode. One or more power source types may be determined 1004 that are delivering power to the pump. The method 1000 may further include monitoring the one or more power sources based on the one or more power source types 1006. A power condition that is indicative of a mode to conserve power may be identified 1008. When the power condition is indicative of a mode to conserve power 1008, a signal may be transmitted to the pump to transition the pump from the first flow mode to a second flow mode that consumes less power 1010. The pump may then be operated at the second flow mode 1012. Thereafter, the method 1000 may include identifying an end to the power condition that is indicative of a mode to conserve power 1014. After identifying an end to the power condition that is indicative of a mode to conserve power 1014, a signal may be transmitted to the pump to transition the pump from the second flow mode to the first flow mode 1016. The pump may then be operated in the first flow mode 1002.

The method 1000 can advantageously sustain VAD operation during low power conditions. Improving the duration of VAD operation during low power has many advantages, such as patient safety, as discussed herein. For example, the method may allow the VAD to continue to operate uninterrupted for longer durations of time while the patient safely secures alternative power sources or recharges existing power sources. Still further, the present invention finds applicability with both external power sources and fully implantable transcutaneous energy transfer systems.

In some embodiments, the first flow mode may be a pulsatile flow mode described above or a variation thereof. For example, the first flow mode may comprise a baseline speed, a transition to a slower speed, then a transition to a speed faster than baseline, and then a return to the baseline speed. In some embodiments, the first flow mode may have an adjustable a base rate, an overshoot, and a diastole. In other embodiments the first flow mode may be a non-pulsatile flow mode. Optionally, the first flow mode may be a continuous speed or constant speed flow mode. The first flow mode may be set by a practitioner depending on the needs of the user or may be a default operational mode for a pump.

In some embodiments, the method 1000 may determine or classify the one or more power source types that are delivering power to the pump 1002. In some embodiments, an implanted blood pump 100 may receive power from a plurality of power sources. As described above, a controller 20 may connect to one or more power sources via a first power cable and a second power cable. For example, some embodiments of a blood pump 100 may be connected to and receive power from a first external rechargeable battery 22 via the first cable and a second external rechargeable battery 22 connected via the second cable. The rechargeable batteries may be lithium ion batteries, for example. Further, in some embodiments, a controller 20 may house a lower capacity rechargeable battery for use in emergency situations, such as when the first and second cables are disconnected from the controller 20, or higher capacity rechargeable battery for pro-longed periods of use. The controller 20 battery may be an emergency backup battery (EBB). Optionally, the blood pump 100 may also be connected to a power module 30 and may receive power directly from an electrically coupled electrical outlet (e.g., AC outlet) coupled with the power module 30 and/or from an EBB housed within the power module 30. The power module 30 may couple to the controller 20 via the first and second cables in some embodiments.

In some embodiments, the controller 20 may include a power monitor module for periodically checking the voltages of one or more attached cables to gather RSOC status information of the one or more attached cables and/or to determine the type of power source connected thereto. In some embodiments, the controller 20 may be configured to determine the type of power source delivering power through the one or more cables and the voltage being supplied therefrom 1004. For example, an analog to digital converter (ADC) may be configured to provide power source information. Optionally a digital to analog converter (DAC) may be provided to verify that the ADC is functioning properly. Further, in some embodiments, an EBB driver may be configured to provide EBB information. A power monitor may be coupled to the ADC and/or EBB driver and be configured to monitor information from the ADC and/or an EBB driver to monitor status of the power supplies of the blood pump.

In some embodiments, RSOC information may be used to identify the type of power source 1004. For example, if the relative state of charge (RSOC) through the first and second cables is greater than 9800 mV, the power monitor may be configured to determine that the power source is a coupled power module 30. When the relative state of charge is greater than or equal to 330 mV and less than or equal to 4600 mV, the power monitor may be configured to determine that the power source for the blood pump 100 is one or more coupled lithium ion batteries 22. When relative state of charge is less than 330 mV or greater than 4600 mV and less than or equal to 9800 mV, the power monitor may identify the power source as unknown. In some embodiments, the power monitor may be further configured to monitor the power status for one or more cables (e.g., the first cable and second cable) attached to the controller via the information from the ADC and/or EBB driver. For example, in some embodiments, when the RSOC information from the associated cables are indicative of disconnected cables, the controller 20 may determine that the system is disconnected from external power sources and that an EBB is powering the pump.

The method may further include monitoring the one or more power sources based on the one or more power source types 1006. For example, the power monitor may periodically analyze information gathered from the ADC driver unit and may provide power related information to other units in the system. For example, the relative state of charge (RSOC) battery levels may be detected and used to determine power sources, power levels, and the average pump power draw level. This information may then be output via a system monitor display or visual indicators (e.g., as power gauge LEDs, or the like) for use by a user or practitioner. Additionally, a power monitor may be configured to analyze readings and report fault conditions to a fault handler as appropriate.

The power monitor may also monitor the one or more power sources by gathering non-RSOC information from the one or more attached cables. Based on this information, the power monitor may be configured to monitor the one or more power sources 1006 by setting and clearing faults related to the voltage levels on each power cable. For example, a power monitor may be configured to handle the following faults: cable disconnected fault, RSOC red fault, RSOC yellow fault, unknown fault, voltage red fault, and voltage yellow fault for the one or more attached cables. The red faults have higher priority over the yellow faults and the voltage faults may have priority over the RSOC faults. In some embodiments, the disconnected fault may have the highest priority and the unknown fault may have a second highest priority.

Accordingly, in some embodiments where the power monitor is configured to set and clear faults related to voltage levels on two power cables, a first power cable and a second power cable, the power monitor may handle the following faults: first cable disconnected fault; second cable disconnected fault; first cable RSOC red fault; second cable RSOC red fault; first cable RSOC yellow fault; second cable RSOC yellow fault; first cable unknown fault; second cable unknown fault; first cable voltage red fault; second cable voltage red fault; first cable voltage yellow fault; and second cable voltage yellow fault.

A power monitor may assign a cable a green status when the power monitor does not assign a yellow, red, unknown, or disconnected status to the cable.

In some embodiments, for example, a power monitor may assign a disconnected fault to a cable when the ADC returns a voltage less than or equal to 1000 mV. Additionally, a cable unknown fault may be reported when ADC returns an RSOC less than 330 mV or greater than 4600 mV and less than or equal to 9800 mV. RSOC yellow faults may be triggered for a connected cable when the RSOC is less than 1930 mV and greater than or equal to 1130 mV. RSOC red faults may be triggered for a connected cable when the relative state of charge is less than 1130 mV. When powered by a power module 30, voltage yellow faults may be triggered for a connected cable when voltage is greater than 10400 mV and less than or equal to 11200 mV and voltage red faults may be triggered for a connected cable when voltage is greater than 1000 mV and less than or equal to 10400 mV. When powered by lithium ion battery 22, voltage red faults may be triggered for a connected cable when voltage is greater than 1000 mV and less than or equal to 13200 mV.

Figure 13:
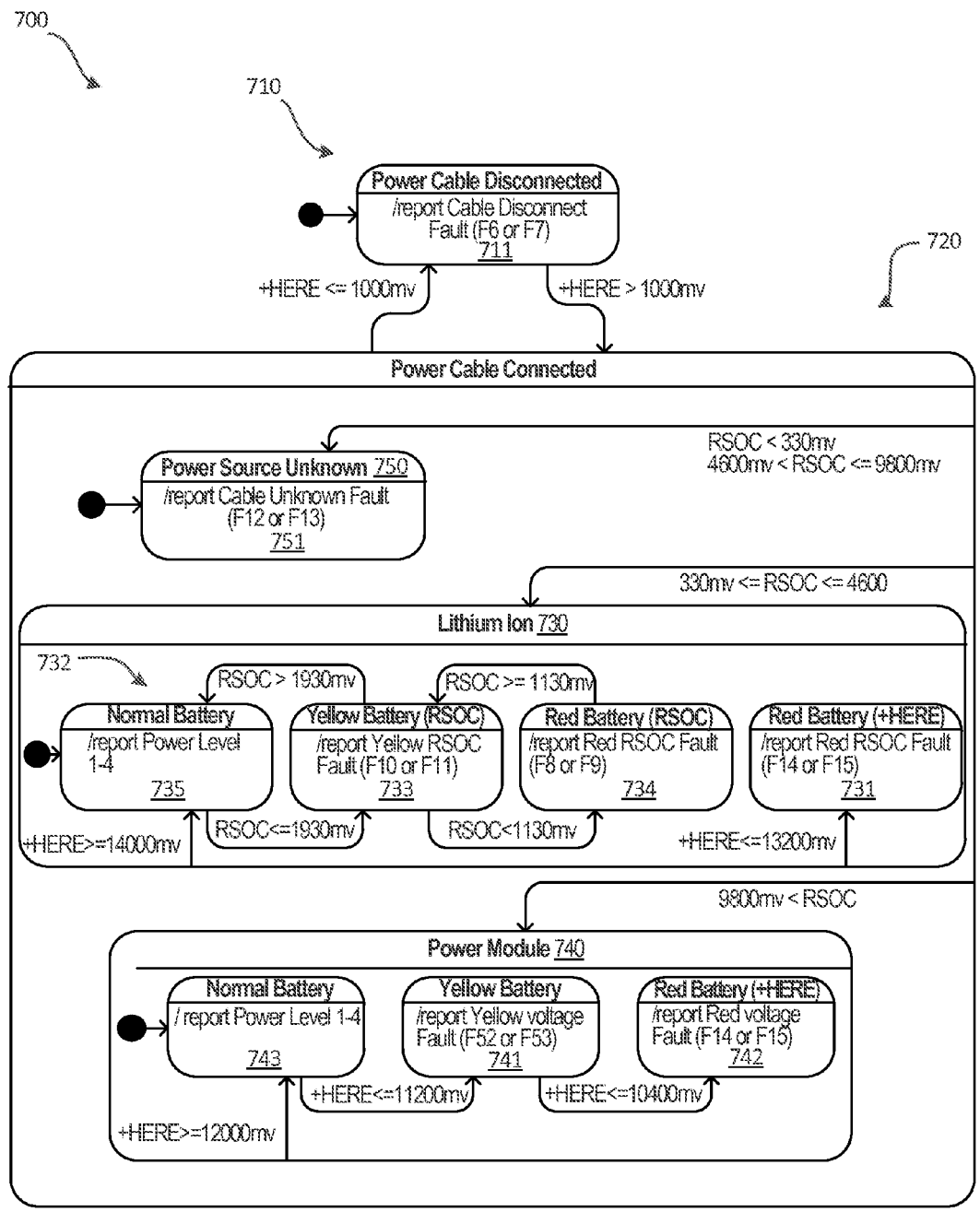
FIG. 13 illustrates a graphical description of exemplary power monitoring rules for a power monitor according to embodiments of the present invention.

FIG. 13 illustrates a graphical description 700 of exemplary power monitoring rules for a power monitor. The power monitor may first determine whether a cable is disconnected 710. When ADC driver returns voltage less than or equal to a disconnect voltage (e.g., 1000 mV in the illustrated embodiment), the power monitor may report a cable disconnect fault for the respective cable 711. When the ADC driver returns voltage greater than the disconnect voltage (e.g., 1000 mV), the power monitor may determine that the cable is connected 712. Once the power monitor determines that the cable is connected, the power monitor may be configured to determine the power source 720.

When the ADC driver returns an RSOC greater than or equal to a minimum battery threshold (e.g., 330 mV in the illustrated embodiment) and lower than a maximum battery threshold (e.g., 4600 mV in the illustrated embodiment), the power monitor may be configured to determine that the power source is a battery 730 (e.g., a rechargeable lithium ion battery, or the like). When the RSOC is greater than a minimum power module threshold (e.g., 9800 mV in the illustrated embodiment), the power monitor may be configured to determine that the power source is a power module 740. When the RSOC is less than the minimum battery threshold (e.g., 330 mV) or greater than the maximum battery threshold (e.g., 4600 mV) but less than or equal to the minimum power module threshold (e.g., 9800 mV), the power monitor may be configured to determine that the power source is unknown 750 and report a cable unknown fault 751.

When the power monitor determines that the power source is a battery 730, the power monitor may be configured to monitor a charge and/or voltage of the battery. When the voltage is less than or equal to a voltage red fault threshold (e.g., 13200 mV in the illustrated example for an exemplary lithium ion battery), the power monitor may be configured to report a voltage red fault status for the power cable 731. When a voltage is greater than or equal to a normal voltage threshold (e.g., 14000 mV in the illustrated example for an exemplary lithium ion battery), the power monitor may be configured to then analyze for RSOC faults of the battery 732.

For example, as illustrated in FIG. 13, when the RSOC is less than or equal to a RSOC yellow fault threshold (e.g., 1930 mV in the illustrated embodiment for a lithium ion battery), the power monitor may report a RSOC yellow fault 733. When the RSOC is less than RSOC red fault threshold (e.g., 1130 mV in the illustrated embodiment for a lithium ion battery), the power monitor may report a RSOC red fault 734. When the RSOC is greater than the RSOC yellow fault threshold (e.g., 1930 mV), the power monitor may determine that the battery is operating normally and may report a power level (e.g., 1-4) 735 to a user via a system monitor, LED power indicators, or the like.

When the power monitor determines that the power source is a power module 740, the power monitor may be configured to monitor a voltage level of the power monitor. When the voltage is less than or equal to a yellow voltage fault threshold (e.g., 11200 mV in the illustrated embodiment), the power monitor may report a yellow voltage fault 741. When the voltage is less than or equal to a red voltage fault threshold (e.g., 10400 mV in the illustrated embodiment), the power monitor may report a red voltage fault 742. When the voltage is greater than the yellow voltage fault threshold, the power monitor may determine that the power monitor is operating normally and may report a power level (e.g., 1-4) 743 to a user via a system monitor, LED power indicators, or the like.

The power monitor may report one fault per cable each time the monitor executes. Faults may remain until a lower priority fault (or no fault) occurs. For example, when going from voltage red fault to disconnected, the red alarm may remain set, but when going from disconnected to voltage red, the disconnect fault may be cleared.

FIG. 14 illustrates a chart describing exemplary alarms for various situations depending on the status of a first cable (e.g., black cable status) and a second cable (e.g., white cable status). As illustrated, a low power hazard condition is triggered when the power monitor reports an unknown, red, or yellow fault for one cable and reports a disconnected, unknown, or red fault for the other cable. When the power monitor reports cable disconnected faults for both cables (white and black), a "no external power" condition is triggered. When one of the cables is green (i.e., not reported as disconnected, unknown, red, or yellow), the system may be configured to trigger at most a low power advisory no matter the status of the other cable. Further, a low power advisory may be issued when the power monitor reports a yellow fault for both cables. When both cables have a green status, no alarms are issued.

The controller 20 may be configured to monitor the status of the system to identify a power condition that is indicative of a mode to conserve power 1008. For example, a power-saving mode may be initiated when the power monitor detects a low power hazard condition and/or a "no external power" condition that persists for an extended duration of time. The extended duration of time may be preset and may be more than 5 minutes, 10 minutes, 15 minutes, 20 minutes or more. The no external power condition may be triggered when the power monitor sets a disconnected fault for each cable. For example, when the controller couples to power sources (e.g., a first battery and a second battery) via a first power cable and a second power cable, the no external power condition may be triggered when the first power cable and the second power cable are disconnected or otherwise assigned a disconnected fault. In such circumstances, a pump 100 may still be powered by an EBB housed within a controller 20. However, due to the relatively short battery life of the EBB, it may be preferable to alert the user and to initiate a power saving mode when a low power hazard condition and/or a no external power condition persists for an extended period of time (e.g., 15 minutes).

The low power hazard condition may be triggered a number of ways as illustrated in FIG. 14. For example, in embodiments where a controller 20 couples to a power source via a first cable and a second cable, a low power hazard condition may be triggered when 1) the status of the first cable is assigned a disconnected, unknown, or red fault (e.g., RSOC red, voltage red) by a power monitor; and 2) the status of the second cable is issued a yellow (RSOC yellow, voltage yellow), red (RSOC red, voltage red), or unknown fault by the power monitor.

In some embodiments, the power-saving mode may be entered when a low power hazard alarm condition or a no external power alarm condition has persisted for the extended duration, individually or cumulatively. For example, when the extended duration for entering the power saving mode is fifteen minutes, the power saving mode may be entered when a low power hazard condition has persisted for seven minutes and a no external power alarm condition persists for eight minutes thereafter. Accordingly, the power saving mode may be initiated after a low power hazard condition persists for an extended duration of time, after a no external power condition persists for an extend duration of time, or after a combined low power hazard condition and a no external power condition for an extended duration of time.

Additionally, the power-saving mode may be initiated when the controller 20 is powered by an emergency backup battery (EBB) and the bus voltage of the EBB falls below a threshold value, (e.g., 10.4 v or the like). This power-saving mode trigger may be advantageous when the pump has been powered by the EBB for an extended period and may benefit from recharging time prior to exiting a power-saving mode.

When the power-saving mode is entered, the controller 20 may be configured to send a command to the VAD 100 to transition from a pulsed mode to a constant or uniform speed mode within a time period from the initiation of power-save mode 1010. The time period may be five seconds in some embodiments. Preferably, the controller may be configured to send the transition command within two seconds from the initiation of the power-saving mode. Optionally, when there is no external power, the controller may be configured to send a command to the VAD to transition from a pulsed mode to a constant speed mode within one second of entering the power-saving mode.

In some implementations, a physician or a user may input a low speed limit for the VAD 100 or a low speed limit may be a default value for the device. The controller 20 may be configured to send a command to the VAD 100 to ramp the speed down to the low speed limit when entering the power-saving mode. In some embodiments, the controller 20 may command the VAD to ramp the speed down to the low speed limit at 50 rpm/15 seconds.

Figure 15:
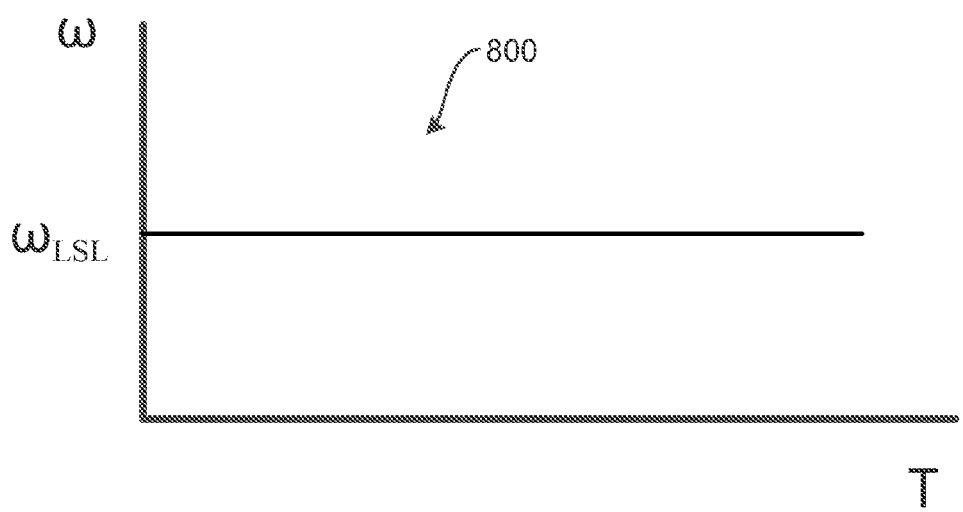
FIG. 15 illustrates an exemplary constant speed mode for operating an implantable blood pump during a power-saving condition.

FIG. 15 illustrates an exemplary constant speed mode 800 for operating an implantable blood pump during a power-saving condition. The constant speed mode 800 may operate the implantable blood pump a constant rotational speed ω throughout the operation of the constant speed mode 800. In the exemplary constant speed mode 800, the constant rotational speed ω is illustrated as rotational speed $\omega_{LSL}$, which corresponds to the rotational speed at the default or previously entered lower speed limit for the user. While illustrated as operating at a constant low speed limit $\omega_{LSL}$, it should be understood that other constant speed modes may be operated at other rotational speeds. It will further be appreciated that in continuous speed mode, the blood pump operational rate is more uniform or steady-state, but may still change over time as suitable in view of changing operational scenarios.

Further, while the above power saving mode is discussed with reference to a controller 20 sending signals to a VAD 100 for transitioning from a pulsatile mode to a constant speed mode, it should be understood that other transitions are possible. For example, a controller 20 may be configured to command an VAD 100 from a first pulsatile mode to a second pulsatile mode when power-saving mode is triggered. The second pulsatile flow mode may consume less power than the first pulsatile mode by, for example, pumping at a lower speed. For example, in some embodiments, a pump may transition to the second pulsatile flow mode from a first pulsatile flow mode by adjusting a base rate speed, an overshoot speed, and/or a diastole speed of the first pulsatile flow mode of the pump. Alternatively, in some embodiments, a controller 20 may be configured to command a VAD 100 to transition from a first constant speed to a second constant speed mode when power-saving mode is triggered. The second constant speed mode may consume less power than the first constant speed mode by providing continuous speed at a lower speed, for example.

When in the power-save mode, and when one or more power-saving mode triggers end (e.g., external power connection) 1014, the controller 20 may then send a signal to the VAD 100 to resume operation according to the prior operational mode 1016. For example, in some embodiments, when the VAD 100 is operating in a power-saving mode and the controller 20 detects a connection to an external power source such as a charged external battery, AC outlet, or the like, the controller 20 may exit power-saving mode and send a signal to the VAD 100 to change speed to the previous operating mode. In some embodiments, the controller 20 may command the VAD 100 to transition from a power-saving continuous flow mode to a normal continuous speed mode or a pulsatile speed mode when one or more of the power-saving triggering conditions ceases. The normal continuous speed mode or the pulsatile flow mode may be the prior operational mode. Optionally, the controller 20 may command the VAD 100 to transition from a power-saving pulsatile flow mode to a normal pulsatile flow mode which may be the prior operational mode prior to the controller entering the power-saving mode.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis, such as where the patient's aortic valve is surgically scaled.

The subject matter and the functional operations described in this specification can be implemented in digital electronic circuitry, in tangibly-embodied computer software or firmware, in computer hardware, including the structures disclosed in this specification and their structural equivalents, or in combinations of one or more of them. The subject matter described in this specification can be implemented as one or more computer programs, i.e., one or more modules of computer program instructions encoded on a tangible non transitory program carrier for execution by, or to control the operation of, data processing apparatus. The program carrier can be a computer storage medium for example, a machine-readable storage device, a machine-readable storage substrate, a random or serial access memory device, or a combination of one or more of them, as described further below. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read only memory or a random access memory or both. The essential elements of a computer are a processing unit for performing or executing instructions and one or more memory devices for storing instructions and data. A computer can also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a pump, a pump controller, or a portable storage device, e.g., a universal serial bus (USB) flash drive or other removable storage module, to name a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Accordingly, other embodiments are within the scope of the following claims.

What is claimed is:

1. A method for controlling an implantable blood pump with an external controller, the method comprising:
   identifying a status of one or more power sources for the implantable blood pump that is indicative of a mode to conserve power; and
   transmitting, from the external controller, a command signal to the implantable blood pump to transition the implantable blood pump from a pulsatile pumping operation to a constant speed operation, the constant speed operation consuming less power than the pulsatile pumping operation; and
   receiving and processing, with electronics of the implantable blood pump, the command signal to transition the implantable blood pump from the pulsatile pumping operation to the constant speed operation;
   wherein identifying the power source status that is indicative of the mode to conserve power comprises:
   identifying a low power hazard condition status;
   identifying a duration of time in which the implantable blood pump is operated in the low power hazard condition; and
   comparing the duration of time to a threshold time period; and
   transmitting the command signal to the implantable blood pump when the duration of time exceeds the threshold time period.

2. The method of claim 1, wherein the low power hazard condition is identified by monitoring a status of a first cable and a second cable coupled to the external controller of the implantable blood pump.

3. The method of claim 2, wherein the first cable and the second cable are assigned:
   a first fault status when: 1) relative state of charge information associated with the respective cable is indicative of a rechargeable battery power source below a first threshold charge, or 2) relative state of charge information associated with the respective cable is indicative of a power module and voltage information is below a first power module threshold voltage;
   a second fault status when: 1) relative state of charge information associated with the respective cable is indicative of a rechargeable battery power source below a second threshold charge, the second threshold charge being lower than the first threshold charge, or 2) relative state of charge information associated with the respective cable is indicative of a rechargeable battery power source and voltage information is below a battery threshold voltage, or 3) relative state of charge information associated with the respective cable is indicative of a power module and voltage information is below a second power module threshold voltage, the second power module threshold voltage being lower than the first power module threshold voltage;
   an unknown fault status when relative state of charge of the respective cable is indicative of an unknown power source;
   a disconnect fault status when voltage information associated with the respective cable is indicative of a disconnected cable; and
   a third status when the first cable or second cable are not assigned a first fault status, a second fault status, an unknown fault status, or a disconnect fault status.

4. The method of claim 3, wherein the low power hazard condition is triggered when the first cable is assigned the first fault status, the second fault status, or the unknown fault status, while the second cable is assigned the disconnect fault status, the unknown fault status, or the second fault status.

5. The method of claim 3, further comprising transmitting a second signal to the implantable blood pump to transition back to the pulsatile pumping operation when the first cable or second cable is assigned the third status or when the first cable and the second cable are assigned the second fault status.

6. The method of claim 1, wherein identifying the power source status that is indicative of the mode to conserve power comprises identifying the power source as an emergency battery which has powered the pump for greater than a threshold time period.

7. The method of claim 6, wherein the threshold time period is at least 15 minutes.

8. The method of claim 1, wherein identifying the power source status that is indicative of the mode to conserve power comprises identifying the power source as an emergency battery which is below a threshold voltage.

9. The method of claim 8, wherein the threshold voltage is equal to or less than 10.4 volts.

10. The method of claim 1, wherein the electronics of the implantable blood pump are on-board the pump.

11. The method of claim 1, wherein the electronics of the implantable blood pump include a processor.

12. The method of claim 1, wherein the electronics of the implantable blood pump execute software for transitioning the implantable blood pump from the pulsatile pumping operation to the constant speed operation in response to the command signal.

13. A method for controlling an implantable blood pump with a controller, the method comprising:
   identifying a status of one or more power sources for the implantable blood pump that is indicative of a mode to conserve power; and
   transmitting a signal to the implantable blood pump from the controller-to transition from a pulsatile pumping operation to a constant speed operation, the constant speed operation consuming less power than the pulsatile pumping operation;
   wherein identifying the power source status that is indicative of the mode to conserve power comprises identifying a disconnection between the controller and one or more external power sources or a low power hazard condition status;
   wherein identifying the power source status that is indicative of the mode to conserve power comprises:
   identifying a duration of time in which the controller is disconnected from the one or more external power sources or a duration of time in which the implantable blood pump is operated in the low power hazard condition; and comparing the duration of time to a threshold time period; and transmitting the signal to the implantable blood pump when the duration of time exceeds the threshold time period.

14. The method of claim 13, wherein the threshold time period is at least 15 minutes.

15. A method of controlling an implantable blood pump with an external controller, the implantable blood pump being powered by one or more power sources, the method comprising:
determining a type of one or more power sources that are powering the implantable blood pump;
identifying an operating condition associated with the type of one or more power sources that is indicative of a mode to conserve power;
transmitting, from the external controller, a command signal to the implantable blood pump to transition the implantable blood pump from a first operational mode to a second operational mode upon the identification of the operating condition associated with the type of one or more power sources that is indicative of the mode to conserve power, the second operational mode consuming less power than the first operational mode;
receiving and processing, with electronics of the implantable blood pump, the command signal to transition the implantable blood pump from the first operational mode to the second operational mode;
wherein identifying the operating condition that is indicative of the mode to conserve power comprises:
identifying a low power hazard condition status;
identifying a duration of time in which the implantable blood pump is operated in the low power hazard condition; and
comparing the duration of time to a threshold time period; and
transmitting the command signal to the implantable blood pump when the duration of time exceeds the threshold time period.

16. The method of claim 15, wherein the external controller determines the one or more power sources as an emergency battery housed within the external controller when the external controller is disconnected from external power sources.

17. The method of claim 16, wherein the operating condition associated with the emergency battery that is indicative of the mode to conserve power comprises a voltage of the emergency battery below a threshold voltage or the emergency battery powering the implantable blood pump a duration of time that exceeds a threshold time period.

18. The method of claim 15, wherein determining the type of one or more power sources comprises determining whether a first cable and a second cable couple one or more external power sources to the external controller.

19. The method of claim 18, wherein determining whether the first cable and the second cable are connected to one or more external power sources comprises:
monitoring voltage information associated with the first cable and the second cable;
comparing the voltage information to a connection threshold;
determining that the first or second cable is connected when the associated voltage information is greater than or equal to the connection threshold;
determining that the first or second cable is disconnected when the associated voltage information is less than the connection threshold; and
reporting a disconnect fault status to the first or second cable when the first or second cable are determined to be disconnected from the external controller.

20. The method of claim 19, wherein the signal is transmitted to the implantable blood pump when the first and second cable are determined to be disconnected from the external controller for a time period greater than greater than or equal to 10 minutes.

21. The method of claim 19, wherein, when the first or second cable are determined to be connected, the one or more power sources may be categorized as an external battery or a power module based on relative state of charge information associated with the first or second cable.

22. The method of claim 21, wherein the one or more power sources are determined to be a rechargeable battery when the relative state of charge information associated with the first or second cable is greater than a minimum battery threshold and less than or equal to a maximum battery threshold.

23. The method of claim 21, wherein the one or more power sources are determined to be a power module when the relative state of charge information associated with the first or second cable is greater than a power module threshold.

24. The method of claim 21, wherein the one or more power sources are determined to be an unknown power source when the relative state of charge information associated with the first or second cable falls outside relative state of charge ranges associated with the external battery and the power module; and
wherein the method further comprises reporting an unknown fault status to the first or second cable when the external power source is categorized as an unknown power source.

25. The method of claim 24, further comprising monitoring relative state of charge information and the voltage information associated with the first and second cables to identify the operating condition that is indicative of a mode to conserve power; and
reporting fault statuses to the first or second cable based on the relative state of charge information and the voltage information.

26. The method of claim 25, wherein reporting fault statuses comprises:
reporting a first fault status to the first and/or second cable when a relative state of charge is less than 1130 mV and greater than or equal to 330 mV;
reporting the first fault status to the first and/or second cable when the external power source is characterized as the rechargeable battery and the voltage is greater than 1000 mV and less than or equal to 13200 mV or when the external power source is characterized as the power module and the voltage is greater than 1000 mV and less than 10400 mV;
reporting a second fault status to the first and/or second cable when the relative state of charge is less than 1930 mV and greater than or equal to 1130 mV;
reporting the second fault status to the first and/or second cable when the external power source is characterized as the power module and the voltage is greater than 10400 mV and less than or equal to 11200 mV; and
reporting a third status to the first and/or second cable when the first and/or second cable is not issued the first fault status, the second fault status, the unknown fault status, or the disconnected fault status.

27. The method of claim 26, wherein the operating condition that is indicative of the mode to conserve power comprises operating the implantable blood pump for a time period greater than 10 minutes when the first cable is assigned the first fault status, the second fault status, or the unknown fault status while the second cable is assigned the first fault status, unknown fault status, or the disconnected fault status.

28. The method of claim 27, further comprising transmitting a second signal to the implantable blood pump to transition back to the first operational mode when the first cable or second cable is assigned the third status or when the first cable and the second cable are assigned the second fault status.

29. The method of claim 15, wherein the first operational mode is a pulsatile operational mode, and wherein the second operational mode is a constant speed operational mode.

30. The method of claim 15, wherein the first operational mode and the second operational mode are pulsatile operational modes, and the second operational mode consuming less power than the first operational mode by operating at a lower flow rate.

31. The method of claim 15, wherein the first operational mode and the second operational mode are constant speed modes, the second operational mode consuming less power than the first operational mode by operating at a lower flow rate.

32. A implantable blood pump system, comprising:
an implantable blood pump configured to supplement or replace the pumping function of a heart and;
an external controller communicatively coupled with the implantable blood pump and configured to identify a status of one or more power sources for the implantable blood pump that is indicative of a mode to conserve power, and transmit a command signal to the implantable blood pump to transition from a pulsatile pumping mode to a constant speed mode, the constant speed mode consuming less power than the pulsatile pumping operation; and
wherein the implantable blood pump includes associated electronics for receiving and processing the command signal to transition the implantable blood pump from the pulsatile pumping mode to the constant speed mode;
wherein the external controller is configured to identify a low power hazard condition status as being indicative of the mode to conserve power;
wherein the external controller is configured to identify a duration of time in which the implantable pump is operated in the low power hazard condition; and
wherein the external controller is configured to compare the duration of time to a threshold time period; and
wherein the controller is configured to transmit the command signal to the implantable blood pump to transition from the pulsatile pumping mode to the constant speed mode when the duration of time exceeds the threshold time period.

33. The system of claim 32, wherein the external controller is configured to couple to one or more external power sources for powering the implantable blood pump and wherein the external controller comprises an emergency battery for powering the implantable blood pump when the external controller is disconnected from the external power source;
wherein the external controller is configured to transmit the signal when the external controller determines that the emergency battery is powering the implantable blood pump for greater than a threshold time period.

34. The system of claim 33, wherein the threshold time period is greater than 10 minutes.

35. The system of claim 32, wherein the external controller is configured to couple to one or more external power sources for powering the implantable blood pump and wherein the external controller comprises an emergency battery for powering the implantable blood pump when the external controller is disconnected from the external power source;
wherein the external controller is configured to transmit the signal when the external controller determines that the emergency battery is below a threshold voltage.

36. The system of claim 35, wherein the threshold voltage is equal to or less than 10.4 volts.

37. The system of claim 32, wherein the external controller is configured to couple to one or more external power sources by a first cable and a second cable, and wherein the external controller is configured to monitor the first cable and the second cable and to report fault statuses to the first cable and the second cable based on relative state of charge information and voltage information associated with the first cable and associated with the second cable; and wherein the low power hazard condition is triggered by one or more fault statuses issued to the first and/or second cable by the external controller.

38. The system of claim 37, wherein the threshold time period is 10 minutes or more.

* * * * *